US012765505B2

(12) United States Patent
Kalisvaart et al.

(10) Patent No.: US 12,765,505 B2
(45) Date of Patent: Oct. 20, 2026

(54) **GENE LEADING TO ToBRFV RESISTANCE IN *S. lYCOPERSICUM***

(71) Applicant: RIJK ZWAAN ZAADTEELT EN ZAADHANDEL B.V., De Lier (NL)

(72) Inventors: Jonathan Kalisvaart, De Lier (NL); Daniël Johannes Wilhelmus Ludeking, De Lier (NL); Alwin Johannes Marinus Roovers, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 496 days.

(21) Appl. No.: 18/151,560

(22) Filed: Jan. 9, 2023

(65) Prior Publication Data

US 2023/0284587 A1 Sep. 14, 2023

Related U.S. Application Data

(63) Continuation-in-part of application No. PCT/EP2021/070104, filed on Jul. 19, 2021.

(30) Foreign Application Priority Data

Jul. 17, 2020 (WO) ................. PCT/EP2020/070347

(51) Int. Cl.
*A01H 6/82* (2018.01)
*A01H 1/00* (2006.01)
(Continued)

(52) U.S. Cl.
CPC ............. *A01H 6/825* (2018.05); *A01H 1/045* (2021.01); *A01H 1/126* (2021.01);
(Continued)

(58) Field of Classification Search
None
See application file for complete search history.

(56) References Cited

U.S. PATENT DOCUMENTS

2020/0077614 A1 3/2020 Ashkenazi et al.
2025/0008903 A1 * 1/2025 Kalisvaart .............. A01H 1/045

FOREIGN PATENT DOCUMENTS

WO 2018/219941 A1 12/2018
WO 2019/110821 A1 6/2019
(Continued)

OTHER PUBLICATIONS

Kabas et al. "Screening of wild tomato species and interspecific hybrids for resistance/tolerance to Tomato brown rugose fruit virus (ToBRFV)" 2022 Chilean J. Agri. Res. 82(1):189-196. (Year: 2022).*
(Continued)

*Primary Examiner* — Amjad Abraham
*Assistant Examiner* — Rebecca Stephens
(74) *Attorney, Agent, or Firm* — Duane Morris LLP; Thomas J. Kowalski

(57) ABSTRACT

The invention relates to a *Solanum lycopersicum* plant that is resistant to ToBRFV, which plant comprises a QTL on chromosome 8 between SEQ ID NO: 1 and 4. The presence of the QTL on chromosome 8 is identified by use of at least one of the markers selected from the group consisting of the SNP presented in SEQ ID NOS: 1 to 42. The QTL is present in the genome of a *Solanum lycopersicum* plant representative seed of which was deposited with the NCIMB under deposit number NCIMB 43637.

5 Claims, 14 Drawing Sheets

Specification includes a Sequence Listing.

qPCR results showing virus titer of material with the individual QTLs of chr 8 and 11, and the combination.

(51) Int. Cl.
*A01H 1/04* (2006.01)
*C12N 15/82* (2006.01)
*C12Q 1/6895* (2018.01)

(52) U.S. Cl.
CPC ....... *C12N 15/8283* (2013.01); *C12Q 1/6895* (2013.01); *C12Q 2600/13* (2013.01)

(56) References Cited

FOREIGN PATENT DOCUMENTS

| | | | | | |
|---|---|---|---|---|---|
| WO | WO-2019110130 | A1 | * | 6/2019 | ........... C12Q 1/6895 |
| WO | 2020/148021 | A1 | | 7/2020 | |

OTHER PUBLICATIONS

NCBI Accession No. XP_015085284; Tobamovirus Multiplication Protein 2A [Solanum pennellii] (Jan. 28, 2019).
NCBI Accession No. XM_015229798; Predicated: Solanum pennellii Tobamovirus Multiplication Protein 2A (Jan. 28, 2019).
Database GenPept Accession No. XP 015085284: tobamovirus multiplication protein 2A [Solanum pennelli] Jan. 28, 2019.
J. O. Oladokun, et al., Tomato brown rugose fruit disease: current distribution, knowledge and future prospects, Plant Pathology (2019) vol. 68, No. 9. p. 1579-1586.
Int'l Search Report and Written Opinion dated Nov. 19, 2021 issued in Int'l Application. No. PCT/EP2021/070104.
1 Notice of Rejection issued Jan. 20, 2026 in counterpart Japanese Application No. 2023-503105.

* cited by examiner

Fig. 1A

Figure 1 – Marker sequences SEQ ID Nos. 1-44
The SNP is present in the sequence on position 101, and is indicated in bold and underscored. For SEQ ID No. 28 the polymorphism is positions 101-104, identifying a deletion of GCC as compared to the SL3_00 reference wildtype sequence TGCCGCT. For SEQ ID No. 30 the polymorphism is positions 101-103, identifying a deletion of G as compared to the Sl3_00 reference wildtype sequence TGGA.

SEQ ID No. 1

TGTAAACTTAACATTAATGTTTACTTAGATATTTTAACTAGATTTAGACACCTAATGTCAGATTTCAGTATGTTAT
TTTGACACTTTTTTACACCATCAACAAAAATATATAATGTAAATATGTTATACTTATTAATAACGTGTAAAATATC
AAACTAAATGATAACACTTATCATTTTGTGTCCAAAATAATACTAAAAT

SEQ ID No. 2

TTTTAYATATTTCACTTAAGGCACCAATGGATCAACACCTTCATATGTATATCACCCAAATTTCTCAATTGACGGC
GGTGAATATTTGCACTTTAGACCTTTGCAAGTCATTTCCTTATTCTGTYGACACTACATTAAAAATGATTTTTAGT
GTCAATTAATTAACGGTAATACTTTCGAAATATATATTTTTAGCAGCAA

SEQ ID No. 3

TTCATCGTATTAATATGCAAAAAAAKTAAATTTATAATACTTTTTCTATAATTTTTGAAAATCTAATTATATTTTTT
AAATATCAAATTAATATAATCTAATTTAATTTTGAAAAATTAATCAAATTGACTTTYAATAAGTGCAACATGATA
CTTAAAAAGTGGATGGAAGAAGTAATCAACTGCAACGGTATGTTTGGAA

SEQ ID No. 4

GATTACTTGTCTAATTAATTATTGATATAATTTTAAGTAGTTTACGAACTAGAGAGTATATTTAAAATAAATAAT
TATTTACTAAAAGAGATTCACTCAATATAAACTATAAATAACAAGATTACAACATGAAGACGTGCAAAGATGTT
AGGCCTTATGATAAAGAATAAGGAATAAAATCTTTTTTAGCATTTCGTTTAG

SEQ ID No. 5

TTAACTAAACAMWTAAAATGTATTTAAAACTAGCTATTCCTTTTAATCAATGTATAATATATGTGACAGTATTA
AACTGGACATAAGATATAAGAAATATAAAAARACTTAGCAATGTTTTAAAATATCTTTAAAAGAATATATAAAT
ATTTGTGATTATTTTGAGCAAATAAATGGTAAACATAGATGGAATATTGATAA

SEQ ID No. 6

AATCAAAATTTTATAAAATTGAACCGAAGAATCAAAAGTCCACTCCTAGTCTTAGGGTCTAAAGARTTTTTTGTA
GGGGAGAATTTGTGGGAGTGAATCTATTTGTACTTCGAGCGAATTGTGTGAGCTTAYTCCTTTTTATCATTTGG
ACTTTTTTTAATAAAGTGGATTGTTCATCTCCTCTYATCAAGTGACCGTATC

SEQ ID No. 7

ARTCATTTTGTTTTATGAGATATAGAAATAAAATTTAATTATATTTTATTCTTCTCARATTCTACGTGTAAAATTA
CCATAAATATAACTATTATTAAGATTGTTTAAGAGAAGAYGTAATGACTTTGCACAAAGTSGTTGTTAATATAA
GGATCCACTTGTCCTCGAACGTAATTCATTGTCAAAATTTTGTCTCTATTT

SEQ ID No. 8

TGAGATATAGAAATAAAATTTAATTATATTTTATTCTTCTCARATTCTACGTGTAAAATTACCATAAATATAACTA
TTATTAAGAKTGTTTAAGAGAAGACGTAATGACTTTGCACAAAGTSGTTGTTAATATAAGGATCCACTTGTCCTC
GAACGTAATTCATTGTCAAAATTTTGTCTCTATTTTCAAACGCGCTTAGA

Fig. 1B

SEQ ID No. 9

AATTATATTTTATTCTTCTCARATTCTACGTGTAAAATTACCATAAATATAACTATTATTAAGAKTGTTTAAGAGA
AGAYGTAATGACTTTGCACAAAGTCGTTGTTAATATAAGGATCCACTTGTCCTCGAACGTAATTCATTGTCAAA
ATTTTGTCTCTATTTTCAAACGCGCTTAGATGCRAGTTTAATTTACCAACT

SEQ ID No. 10

TCATTTTTTAAAATAATATTTATATATTTRTAAATTATGTAAAAAGATAATATAAGTCAAAATAATTGGCAATTCA
AAATGGTTGAAAGATATATAAAAATTTCACGATAAAAATAATAATTGAAATCTSAACATCCAAAAAAAATCACA
TAATTAAGACGGAGGAGAAAATATCATCTTTTTAAATTTCAATTATATAAC

SEQ ID No. 11

RTAAATTATGTAAAAAGATAATATAAGTCAAAATAATTGGCAATTCAAAATGGTTGAAAGATATATAAAAAKTT
CACGATAAAAATAATAATTGAAATCTGAACATCCAAAAAAAATCACATAATTAAGACGGAGGAGAAAATATCA
TCTTTTTAAATTTCAATTATATAACTATACTGAATATATTATTATTACCACGGT

SEQ ID No. 12

TTTGTTTTGATTGTATCGTATAGTATTATAATTTATAAATTTASTAAAATATCGTTAATCATTCTAGGGAATGAGG
TTTGACTAGATTTAAATAATTAAGGTAAAGGGTAAAATAGTATTTTGAAATATTACGTAAAGATATAATTGGAA
AAAGAAATTAAGTAACAATGCGAAAACACCAAATCGGTTGTTCCATAAAAT

SEQ ID No. 13

AAAAATTCTTTGAATGAAGTAGAATTCTAWATGATAAAAATTTAAAATAATTAAATTTTAATGAAATACACTGA
CAAATAGGGCTGTGTATCGATCGATTCGGTTTAATTTTRAAGTTTATCGGATTGGCTTATTGGTTATYGGTTTAT
AATGATGCTAAATCATTATAGAACCATTAARATATTGACTTATCGGTTATTG

SEQ ID No. 14

AATGAAGTAGAATTCTAWATGATAAAAATTTAAAATAATTAAATTTTAATGAAATACACTGACAAATAGGGCT
GTGTATCGATCGATTSGGTTTAATTTTAAAGTTTATCGGATTGGCTTATTGGTTATYGGTTTATAATGATGCTAA
ATCATTATAGAACCATTAARATATTGACTTATCGGTTATTGGTTTATSGGTTT

SEQ ID No. 15

ATTTTRAAGTTTATCGGATTGGCTTATTGGTTATYGGTTTATAATGATGCTAAATCATTATAGAACCATTAARAT
ATTGACTTATCGGTTATTGGTTTATGGGTTTTTGATCGTTATCGGTTTAACCGTTAAGATTTGAMTCAAAARAA
AAAATATTGAAAATCACTTAGAAACAAGGTGACAAATCAAATAAACCATGCA

SEQ ID No. 16

TTTTAATTTAATATTGGTATATATAAAAGTTGGACCTCCTAAAATAATTTAGTAAGACACAATAGAGTTGGCAAT
AGCTAGGGCATCCCTACACTTTGTCTGGGTTTGATTTCCCGCGGGATGTTTCATTTTTCTTTAATTATTTTTGACA
ATTTTATTATTAAAAAAACATGCTTASTCTTAACATAAACATTTAGTAGT

SEQ ID No. 17

CACAAATTATTAGATTCATTTCTGAACTATTAACAGCCTTGAAAACACCTCTCTACTAAYATAGCAAGCGATCTC
AAACTCTTATATGAAYATGAGACTTGTAATAAAAAGCTGAGAGAAGTGTTGAAAACACTCCTAAAKTAGTGAT
GTACTGCATTCATGATGCAAGATCGGRGATGTATTTTATCCTTCAGGGTTGYC

Fig. 1C

SEQ ID No. 18

GAAAACACCTCTCTACTAAYATAGCAAGCGATCTCAAACTCTTATATGAAYATGAGACTTRTAATAAAAAGCTG
AGAGAAGTGTTGAAAACACTCCTAAAGTAGTGATGTACTGCATTCATGATGCAAGATCGGRGATGTATTTTATC
CTTCAGGGTTGYCCAGTGTTACCTCGCCTATTTAGTTTGCGCTCTATTGAGTA

SEQ ID No. 19

AATAAARTAGTACACATTGTTTGGTCAAACAATTTGGTGATTTTTTGAAAATATATCTTCAAAAATTAATCAAAC
TTCAAAATCTGGTCRTGAAATATCAATTTCATTCATAGAATTTTAATTTATTTGCAGAGAAAATGTAGGGATAAG
AGTYTGAAAAATATCTCAATTTTGATCGAATTTGTTCTTGCGATACTTAAC

SEQ ID No. 20

GCCAGATGACAGACTTTGTGGATGCTTACTCTCAGTTGTGTCCTACTGCAAGGGCGACGATGCAGATAAGGTC
CTTGCTTGTCTACAACAAGCTAACCCAAGATTGGTAACCTTTGTCAAGATGCTAGAAGATGAGAGCACTAGCTA
TGACATTGTGAAAGAAGAGTTCAGGTCCATACTGACTAATACATCAGATGATGC

SEQ ID No. 21

ATTGTGAAAGAAGAGTTCAGGTCCATACTGACTAATACATCAGATGATGCTAGAAGGCCCTTCTGTAATTGTCT
AATTGATATATGCAGAAAGAGAAATCACGCAGAGAGGGCTCACGAGCTTCTATACTTGGGAACTGTATATGGA
CTATACCCAGGTTTACATACTAAGACACCAGAAGAATGGCGATTRAACGTCCGA

SEQ ID No. 22

TAAATATAAATAAATCGTTCAAGTTTGTTACGATCCAAAAAYGAGGCTTGARTGRCACTCACACTTATCCTACTA
TGTGAGCGAACCAACCCATCTAAAYTCCAACATTTCAAAACATAATAGACAGAATATAATGYGGAAGACTTAAA
ACTCATTAACGAAGTCAATAATTAACTTCTAAAACTCAAAACTTATCATTAT

SEQ ID No. 23

TTAATARGACTCCTTACAAGCGTTGTTTCTATCTACTATTATCTAAAAATAATCAAGTTATTAATGACCGGACGA
AACAAAGAAATAACCCCTCATGTGCGAAATTATAGAAGATCCCCTTTAAGATCAAACAATTCCATMRAATTGA
GTATGATTGTATGTGTGATAGCATCTACTATACCAGGAATATCAATGAACCCG

SEQ ID No. 24

AAGAGGCCGTGGTAGAGGTCGTGGGAGGACGTCCTCTAGAGGAAGGGGACGAGCACCTAGCCCATCTGATA
CTAGGGCGGTGACTCCTCCACCGACTGAATAAGTAGTAATAGAAGGGGAGGATGGGGAAAATGAACAAGTAC
AGAATGAGGAATTACCACCCCAACCTACCCCAGAAATGATCAATCAGGTTCTTGCTTA

SEQ ID No. 25

TAACTTATATTTGTAAATAAATCTCATGTTTAACTCAAACTCAAAAAGCAACSACACTATCATAAAAATAAAAAG
TCACTCATCCTTAAAGGGACAATTCCGGACTCATTAAATTCCTCGAACTCAATCTGAATCTAGACATCTAATGCA
TAAACAATTTAATATAAAAAGTCCTACACCAAAAAATAAAAAATGGAATAA

SEQ ID No. 26

GCTGGTGGCCTATTGTTGATCAGTGGCTGTCGGATTTGTTGTCTGGGACCACCTATGTACTCATCATCACTATC
ATARTCTGCTGGTCTGTTTGCTGCCCCTACTACGAGGGCCAATAAGAATATAAGAGCCTGCAACTCATGTAAAC
RGACGAAACTGAGAGACTYGGAGAAAATTAAGACAAACAATTTTCAGGTNNNN

Fig. 1D

SEQ ID No. 27

TCGTTTCAAAGTTGCCCGTTTTATCCCTTGGAATTTCCTGACAAAGACTTTCATCACTTTTCTGACAACAAAGTAT
AGTWTGAAAGTGAAGTCGTGAGTGCGAAAACACTTACATCTTTCCAGCTTTTATCAAAGAATATAAAACCAGC
AGCACCTAGCTCTACCAAGATCAACAAGAAAATCAACATGGAGTACTGTTCC

SEQ ID No. 28 - InDel

TATGTGGGCTGTATATTTTTTAAATTTTCCCATAAATAATAAATCAAGAAGACTGAACAAATGATAAGGATACA
CAACTCAGGCAGCAACCATTCCTTGTTGCTCCAATACAACCACAGCAAGATACAACTACAAGAACTGCTCCAAT
ACCAATAAACAAATATATGAACCTGCGACATAACAAATGGGTCAATGCTTCAT

SEQ ID No. 29

TRCAAATCATGTAGTCAAGTTCTGAGAATTCACACCCACTGACCACTCAAAACTTGGAAAATATTATGAGACTC
TGTTAATAATTCAATAWTGGACAAGCCCAAACAGGTGAAGAMCATATATAGTTCCTTTTTCTTATTTATACTTC
CATGTTTCTTTAGCTCTACACCTRGGAAACATATGATTCAACCTTCGCATATA

SEQ ID No. 30 - InDel

AGAGGATGTAAYAGAATGAACTCTCAGTATTTTTAACTGGTTCAAGACTACTTTGGRTTTTCAGAGATTTTAACT
CAATAAGTTCCCTAGGGAAAAGAGATGAATGTGATTCTTTATCTAGTGTAATAGTTCTTGGAGATTTTATTGAT
TATCCGTTGACTGATGATAAGTTCTCCAAATCAAGGAGTCAAAGTGAAGAT

SEQ ID No. 31

TGTATATCTRGMGAGCGAGATTAAGAGAGGGATGAAAGAGGCAAGTGTGATTGGGAGAGAGAGGAGAGAG
ACTAATTGTATTTGTATATCTTTCATATAATTGTATGTATAAATGTACAATTTGTATTTGTATATGGATTAGCAAC
CTAATTACAACTAAAATTAAGTTGTGAGTCGTAATTAATTCAAACTATAGCTACA

SEQ ID No. 32

AATTTGTATAAAATGAGAAAGAGAGAAAGATAAAAGAGACTTGACAAGGAATATACAATTRAATCGAATTGTA
TAAAATGAGAAAGAGAGAAAGTAAATATAWTTTGAAAATTGTATAAGACGAGAAAGAGAGAAGGGCAAAAG
AAASTGGGYAGAGGAGTATTTTTATTGTATAATTATAATTGTWTAGGACGAAAATAT

SEQ ID No. 33

AGAGAAAGTAAATAYAWTTTGAAAATTGTATAAGACGAGAAAGAGAGAAGGGCAAAAGAAASTGGGYAGAG
GAGTATTTTTATTGTATAATTATAATTGTTTAGGACGAAAATATATGTACGTGCATGTGTATATACAATTTTCTC
ACGCTTTATAYAAACAGAAAYGCAATTTATACATTTCGCTTCTGTTTGTACAAGT

SEQ ID No. 34

AATATACATCAATTTTTTATATTAYTTTTCATATAGTGTTTTTAAATATTTTTATTTTCAATRATATTTCTCGTAACA
TAGCCACATATCTAATAAAATACTTTTATTTTTGTAATTTTTAATTTTTAAATACGAGGGTTTGTGACTGACCAAC
RTACSGACTACTCTACCACGTATATACAACATAGTTGGAAAGAATTT

SEQ ID No. 35

CAAAGCTAAATCCTCCCCACTACTCCATCCACTCTCCACCGCCTTTTTYGCCTCCACATTTTCGAAATCAGCCTCA
TTTCCACCCTCAGCTCTCTTATCAGCYGTTTTCCTGTCCTTCAAAAACCTCTGATAGGAATCCCCATCACTCATTTT
CTTCTCACCCAATTCTTTAGATTTCTTAATCACACTTTCCACTTTGTA

Fig. 1E

SEQ ID No. 36

TCTTGTTGGTTGTTATATTTTCAACATTGTTTTCTTTTTCTTTGTACTTGAATTTGTTGTTATTAATCGAACATCTTT
GAAAAACAATCTATCTACCTCGGCAAGGTAATGATATGATTCGTCTATATTCTACCATCTTCGAATCGTGCTTAT
GGAATTTCACGCTAAGGAAACCTTTTCAATACATGAGAAGCGCAGTGT

SEQ ID No. 37

TTTCTGGCAGGGCTGGTGGTTCTTTTGATGATAGGAGGTTTCTAGACGATAGATTTTCAAGGGATGGTGTTTAT
CCCCGGGGTGCCTATCACCGTGATATTCTGGATGGAGAGCACTACCCTCATCCACCAGCAGCAGTTGGACACT
GGCCTCAGACAAGGAGGAGAAGTTATGAAGAAGTGTACCCTGTGGAGAGGGATT

SEQ ID No. 38

CCGATACGATAGAAGTGAGAGACGAAGAGATCGTGATGATAAAAGATACCATGACAATTATTCTGTGGTATGT
TTCCTGTTTCTTATGTTGCACTTCCCAGTTGCTTTTATGTTTGGAGGGGCTCATGGCTTCTGTTATTTTAATGCAG
GCTCCTTCAGCGACTGTTGTTGTCAAAGGCCTTTCACAAAAAACTACTGAAG

SEQ ID No. 39

TATTATTGCTTGGGCTTCAAGATCGGGACTCAACATTCAGAAGAGGTGTTTTTGATCCAACTCCTTTCCCCCCTG
GTGTYGGAGGTGGACGTAGTGCAGAAGCGAATAGTCAGAGCTTTGAGGTTATCACGGCTGACAGGGCTATAG
ACGAGAGTAAYGTGGGCAATCGTATGCTTCGCAACATGGGATGGCAGGAGGGCT

SEQ ID No. 40

TTCAACACCCTTTAGCTGCAGGTAGAGTTATGATGAAGCTCTGTTCTTCACAATCCACTTTTCCTCATGCTGTAA
AGATTTTTGAGAATCTTGAATACCCAGATGCTTTTATTTGTAATACAGTTATGAAATGTTATGTGAATTTCGATG
ACCCGGAAAAGGGTTTGGTGTTTTATTCTGATCAGATGGTTAAAAATGGGA

SEQ ID No. 41

TACAAATAATGTCGTGTATGGAATAAACTTGCTTACAATTCAATGGTTCTATGAAACAGAAATTAGGTAAAATC
TGTTCTRTAGTTTGTTAAGTATATTGTAAAAATAAAATTTCTTTATATGTGGTTAATAGTYATTAGTTTGGCCGTC
CTAATGCATTTTATTCGTTTGATTAAGATTTTCTTTTCATGTATTTGTATA

SEQ ID No. 42

CCAATTTTATAAAATGAGATAGTTCCTCAGTATTCCGTCACTGCTTTTGTTTAAGCTTCAGTTTCCACTAGCAAAC
TTTACATTGTTATGCTCCATATTCGTAATAATCCATGAACTTAACTGTTTACCGCTCTTTCCTCATTGAGAAATGG
TTTAAAACATATAACTTGTACTTTTCGCTGCAAACATATTACATTGTTT

SEQ ID No. 43

TACAGAAGACACAAAATACTTCACACCAGACTAAATTACACAGACAAGCACAATCATCAGTCCTCCCAAATTTA
CAGAAGACCATATCATCACATTATGGCACAACCCTTCCTTTCCTCTTGCGGCTGTGCGGCWGTTGGCGGATATC
TGTTCGACTCCGATGGGTTGTAAGTAAACTCTGATGTGTCAAGTCCATACTGG

SEQ ID No. 44

AATAAAGCAATCAACAGAAAGCAAACCTTTTCCCTCATACGTGTACTCCAYGCATCATTTCTACTTGGACGATTA
TCAAGAGTAGCAGTAACAGGGACACTAGTTGCAGGATTTGCTGGTGGCCTATTGTTGATCAGTGGCTGTCGGA
TTTGTTGTCTGGGACCACCTATGTACTCATCATCACTATCATARTCTGCTGGT

Fig. 4

Figure 4 – Marker haplotypes and phenotypes of recombination lines

| Pedigree | Expected if cluster left of SL005 contains causal gene | Expected if Tom2a is causal gene | Expected if Solyc08g077230.3.1 is causal gene | OBSERVED ToBRFV phenotype | Generation | SL001 - SEQ ID No. 22 | Solyc08g077180.2 | Solyc08g077170.3 | SL002 - SEQ ID No. 75 | SL003 | Solyc08g077160.3 | Solyc08g077190.1 | Solyc08g077200.3 | Solyc08g077210.3 | SL004 | SL005 | Solyc08g077220.3 | SL006 - SEQ ID No. 26 | SL007 - SEQ ID No. 29 | SL008 - SEQ ID No. 31 | SL009 - SEQ ID No. 32 | SL010 | SL011 | Solyc08g077230.3 | SL012 - SEQ ID No. 34 | SL013 |
|---|---|---|---|---|---|---|---|---|---|---|---|---|---|---|---|---|---|---|---|---|---|---|---|---|---|---|
| | | | | | Chromosome SL3.00 > | 61.175.582 8 | 61187788..61188051 8 | 61201639..61208886 8 | 61.202.144 8 | 61.208.138 8 | 61208597..61215801 8 | 61217182..61217481 8 | 61222622..61228579 8 | 61229146..61234179 8 | 61.235.008 8 | 61.245.722 8 | 61250475..61256857 8 | 61.251.554 8 | 61.253.498 8 | 61.257.969 8 | 61.258.594 8 | 61.262.045 8 | 61.262.164 8 | 61251820..61257676 8 | 61.258.020 8 | 61.279.928 8 |
| (TB2*GNL3951) - 01 | Fixed R | Segr | Segr | Segr | F2 | B | | | B | B | | | | | B | H | | H | H | H | H | H | H | | H | H |
| (TB2*GNL3951) - 02 | Segr | Fixed R | Fixed R | Fixed R | F2 | H | | | H | H | | | | | H | B | | B | B | B | B | B | B | | B | B |
| (TB2*GNL3951) - 03 | Segr | Fixed R | Fixed R | Fixed R | F3 | H | | | H | H | | | | | H | H | | B | B | B | B | B | B | | B | B |
| (TB2*GNL3951) - 04 | Segr | Fixed S | Fixed S | Fixed S | F2 | B | | | B | H | | | | | H | A | | A | A | A | A | A | A | | A | A |
| (TB2*GNL3951) - 05 | Segr | Fixed S | Fixed S | Fixed S | F2 | H | | | H | H | | | | | H | A | | A | A | A | A | A | A | | A | A |
| (TB2*GNL3951) - 06 | Segr | Fixed R | Fixed R | Fixed R | F3 | H | | | H | H | | | | | H | B | | B | B | B | B | B | B | | B | B |
| (TB2*GNL3951) - 07 | Segr | Segr | Fixed R | Segr | F3 | H | | | H | H | | | | | H | H | | H | H | H | H | B | B | | B | B |
| (TB2*GNL3951) - 08 | Fixed R | Segr | Segr | Segr | F3 | B | | | B | B | | | | | B | H | | H | H | H | H | H | H | | H | H |
| (TB2*GNL3951) - 09 | Fixed R | Segr | Segr | Segr | F3 | B | | | B | B | | | | | B | H | | H | H | H | H | H | H | | H | H |
| (TB2*GNL3951) - 10 | Segr | Fixed R | Fixed R | Fixed R | F3 | H | | | H | H | | | | | H | B | | B | B | B | B | B | B | | B | B |
| (TB2*GNL3951) - 11 | Fixed R | Segr | Segr | Segr | F3 | B | | | B | B | | | | | B | B | | H | H | H | H | H | H | | H | H |
| (TB2*GNL3951) - 12 | Fixed R | Segr | Segr | Segr | F3 | B | | | B | B | | | | | B | H | | H | H | H | H | H | H | | H | H |

Fig. 5A

Figure 5 - Tom2a CDS sequences

SEQ ID No. 45

>Tom2a_GNL.3951_R 43637 minus-strand

ATGGCGTGCAAAGGGTTTTGGGAGTGCTTGTTGAAGCTCTTGAACTTTTTGTTGACCCTTGTTGGTTTGAC
AATGGTGGGGTATGGTATTTATCTATTTGTTGAGTACAAAAATCATTCACACTCCGGAGATGATTACCCAG
TTGCACCACCTATGAGTGGTGACATGATAGAGTTTGGTCGTCCAATGCTGATGGCTGTATCGTTGGCTGAA
AACATATTTGATAAACTTCCAAAACCTTGGTTCATATATTTGTTTATTGGTATTGGAGCAGTTCTTGTAGT
TGTATCTTGCTGTGGTTGTATTGGAGCAACAAGGAATGGTTGCTGCCTGAGTTGTTACTCCATGTTGATTT
TCTTGTTGATCTTGGTAGAGCTAGGTGCTGCTGGTTTTATATTCTTTGATAAAAGCTGGAAAGATGAAATT
CCAAGGGATAAAACGGGCAACTTTGAAACGATCTATGACTTTCTGGATGACCACTGGAAGATTATTAAGTG
GGTTGCCCTTGGTGCTGTTATATTCGAGGCTCTTATATTCTTATTGGCCCTCGTAGTAGGGGCAGCAAACA
GACCAGCAGATTATGATAGTGATGATGAGTACATAGGTGGTCCCAGACAACAAATCCGACAGCCACTGATC
AACAATAGGCCACCAGCAAATCCTGCAACTAGTGTCCCTGTTACTGCTACTCTTGATAATCGTCCAAGTAG
AAATGATGCATGGAGTACACGTATGAGGGAAAAGTATGGACTTGACACATCAGAGTTTACTTACAACCCAT
CGGAGTCGAACAGATATCCGCCAACAGCCGCACAGCCGCAAGAGGAAAGGAAGGGTTGTGCCATAATGTGA

SEQ ID No. 47

>tom2a_SL3_00_S minus-strand

ATGGCGTGCAAAGGGTTTTGGGAGTGCTTGTTGAAGCTCTTGAACTTTTTGTTGACCCTTGTTGGTTT
GACAATGGTGGGGTATGGTATTTATCTATTTGTTGAGTACAAAAATCATTCACACTCCGGAGATGATT
ACCCAGTTGCACCACCTATGAGTGGTGACATGATAGAGTTTGGTCGTCCAATGCTGATGGCTGTATCG
TTGGCTGAAAACATATTTGATAAACTTCCAAAACCTTGGTTCATATATTTGTTTATTGGTATTGGAGC
AGTTCTTGTAGTTGTATCTTGCTGTGGTTGTATTGGAGCGGCAACAAGGAATGGTTGCTGCCTGAGTT
GTTACTCCATGTTGATTTTCTTGTTGATCTTGGTAGAGCTAGGTGCTGCTGGTTTTATATTCTTTGAT
AAAAGCTGGAAAGATGAAATTCCAAGGGATAAAACGGGCAACTTTGAAACGATCTATGACTTTCTGGA
TGACCACTGGAAGATTATTAAGTGGGTTGCCCTTGGTGCTGTTATATTCGAGGCTCTTATATTCTTAT
TGGCCCTCGTAGTAAGGGCAGCAAACAGACCAGCAGACTATGATAGTGATGATGAGTACATAGGTGGT
CCCAGACAACAAATCCGACAGCCACTGATCAACAATAGGCCACCAGCAAATCCTGCAACTGGTGTCCC
TGTTACTGCTACTCTTGATAATCGTCCAAGTAGAAATGATGCGTGGAGTACACGTATGAGGGAAAAGT
ATGGACTTGACACATCAGAGTTTACTTACAACCCATCGGAGTCGAACAGATATCCGCCAACTGCCGCA
CAGCCGCAAGAGGAAAGGAAGGGTTGTACCATAATGTGA

Fig. 5B

CDS Alignment

Query: Tom2a_S CDS Length: 855
Sequence ID: Tom2a_R CDS Length: 852
Range 1: 1 to 852

Score:1526 bits(826), Expect:0.0,
Identities:846/855(99%), Gaps:3/855(0%)

```
Sl3_00 1    ATGGCGTGCAAAGGGTTTTGGGAGTGCTTGTTGAAGCTCTTGAACTTTTTGTTGACCCTT  60
            ||||||||||||||||||||||||||||||||||||||||||||||||||||||||||||
GNL_R  1    ATGGCGTGCAAAGGGTTTTGGGAGTGCTTGTTGAAGCTCTTGAACTTTTTGTTGACCCTT  60

Sl3_00 61   GTTGGTTTGACAATGGTGGGGTATGGTATTTATCTATTTGTTGAGTACAAAAATCATTCA  120
            ||||||||||||||||||||||||||||||||||||||||||||||||||||||||||||
GNL_R  61   GTTGGTTTGACAATGGTGGGGTATGGTATTTATCTATTTGTTGAGTACAAAAATCATTCA  120

Sl3_00 121  CACTCCGGAGATGATTACCCAGTTGCACCACCTATGAGTGGTGACATGATACAGTTTGGT  180
            ||||||||||||||||||||||||||||||||||||||||||||||||||||||||||||
GNL_R  121  CACTCCGGAGATGATTACCCAGTTGCACCACCTATGAGTGGTGACATGATACAGTTTGGT  180

Sl3_00 181  CGTCCAATTGCTGATGGCTGTATCGTTGGCTGAAAACATATTTGATAAACTTCCAAAACCT  240
            ||||||||||||||||||||||||||||||||||||||||||||||||||||||||||||
GNL_R  181  CGTCCAATTGCTGATGGCTGTATCGTTGGCTGAAAACATATTTGATAAACTTCCAAAACCT  240

Sl3_00 241  TGGTTCATATATTTGTTTATTGGTATTGGAGCAGTTCTTGTAGTTGTATCTTGCTGTGGT  300
            ||||||||||||||||||||||||||||||||||||||||||||||||||||||||||||
GNL_R  241  TGGTTCATATATTTGTTTATTGGTATTGGAGCAGTTCTTGTAGTTGTATCTTGCTGTGGT  300

Sl3_00 301  TGTATTGGAGCGGCAACAAGGAATGGTTGCTGCCTGAGTTGTTACTCCATGTTGATTTTC  360
            |||||||||||   ||||||||||||||||||||||||||||||||||||||||||||||
GNL_R  301  TGTATTGGAGC---AACAAGGAATGGTTGCTGCCTGAGTTGTTACTCCATGTTGATTTTC  357

Sl3_00 361  TTGTTGATCTTGGTAGAGCTAGGTGCTGCTGGTTTTATATTCTTTGATAAAAGCTGGAAA  420
            ||||||||||||||||||||||||||||||||||||||||||||||||||||||||||||
GNL_R  358  TTGTTGATCTTGGTAGAGCTAGGTGCTGCTGGTTTTATATTCTTTGATAAAAGCTGGAAA  417

Sl3_00 421  GATGAAATTCCAAGGGATAAAACTGGCAACTTTGAAACGATCTATGACTTTCTGGATGAC  480
            ||||||||||||||||||||||||||||||||||||||||||||||||||||||||||||
GNL_R  418  GATGAAATTCCAAGGGATAAAACTGGCAACTTTGAAACGATCTATGACTTTCTGGATGAC  477

Sl3_00 481  CACTGGAAGATTATTAAGTGGGTTGCCCTTGGTGCTGTTATATTCGAGGCTCTTATATTC  540
            ||||||||||||||||||||||||||||||||||||||||||||||||||||||||||||
GNL_R  478  CACTGGAAGATTATTAAGTGGGTTGCCCTTGGTGCTGTTATATTCGAGGCTCTTATATTC  537

Sl3_00 541  TTATTGGCCCTGGTAGTAAGGGCAGCAAACAGACCAGCAGACTATGATAGTGATGATGAG  600
            |||||||||||||||||| |||||||||||||||||||||||| ||||||||||||||||
GNL_R  538  TTATTGGCCCTGGTAGTAGGGGCAGCAAACAGACCAGCAGATTATGATAGTGATGATGAG  597

Sl3_00 601  TACATAGGTGGTCCCAGACAACAAATCCGACAGCCACTGATCAACAATAGGCCACCAGCA  660
            ||||||||||||||||||||||||||||||||||||||||||||||||||||||||||||
GNL_R  598  TACATAGGTGGTCCCAGACAACAAATCCGACAGCCACTGATCAACAATAGGCCACCAGCA  657

Sl3_00 661  AATCCTGCAACTGGTGTCCCTGTTACTGCTACTCTTGATAATCGTCCAAGTAGAAATGAT  720
            ||||||||||| ||||||||||||||||||||||||||||||||||||||||||||||||
GNL_R  658  AATCCTGCAACTAGTGTCCCTGTTACTGCTACTCTTGATAATCGTCCAAGTAGAAATGAT  717

Sl3_00 721  GCGTGGAGTACACGTATGAGGGAAAAGTATGGACTTGACACATCAGAGTTTACTTACAAC  780
            || |||||||||||||||||||||||||||||||||||||||||||||||||||||||||
GNL_R  718  GCATGGAGTACACGTATGAGGGAAAAGTATGGACTTGACACATCAGAGTTTACTTACAAC  777

Sl3_00 781  CCATCGGAGTCGAACAGATATCCGCCAACTGCCGCACAGCCGCAGGAGGAAAGGAAGGGT  840
            |||||||||||||||||||||||||||| |||||||||||||||||||||||||||||||
GNL_R  778  CCATCGGAGTCGAACAGATATCCGCCAACAGCCGCACAGCCGCAGGAGGAAAGGAAGGGT  837
```

Fig. 5C

```
SL3_GQ 841   TGTACCATAATGTGA   855
             ||| |||||||||||
GNL_R  838   TGTGCCATAATGTGA   852
```

Fig. 6

Figure 6 – Tom2a protein sequences

SEQ ID No. 46
>Tom2a_GNL.3951_R 63637
MACKGFWECLLKLLNFLLTLVGLTMVGYGIYLFVEYKNHSHSGDDYPVAPPNSGDMIEFGRPMLMAVSLAE
NIFDKLPKPWFIYLFIGIGAVLVVVSCCGCIGATRNGCCLSCYSMLIFLLILVELGAAGFIFFDKSWKDEI
PRDKTGNFETIYDFLDDHWKIIKWVALGAVIFEALIFLLALVVGAANRPADYDSDDEYIGGPRQQIRQPLI
NNRPPANPATSVPVTATLDNRPSRNDAWSTRMREKYGLDTSEPTYNPSESNRYPPTAAQPQSERKGCAIM

SEQ ID No. 48
>Tom2a_SL3_00_S
MACKGFWECLLKLLNFLLTLVGLTMVGYGIYLFVEYKNHSHSGDDYPVAPPNSGDMIEFGRPMLMAVSLAE
NIFDKLPKPWFIYLFIGIGAVLVVVSCCGCIGAATRNGCCLSCYSMLIFLLILVELGAAGFIFFDKSWKDE
IPRDKTGNFETIYDFLDDHWKIIKWVALGAVIFEALIFLLALVVRAANRPADYDSDDEYIGGPRQQIRQPL
INNRPPANPATGVPVTATLDNRPSRNDAWSTRMREKYGLDTSEPTYNPSESNRYPPTAAQPQSERKGCTIM

Protein alignment

Query: Tom2a proteins Length: 284

>unnamed protein product
Sequence ID: Query_10407 Length: 283
Range 1: 1 to 283

Score:577 bits(1486), Expect:0.0,
Method:Compositional matrix adjust.,
Identities:280/284(99%), Positives:280/284(98%), Gaps:1/284(0%)

```
SL3_00 1     MACKGFWECLLKLLNFLLTLVGLTMVGYGIYLFVEYKNHSHSGDDYPVAPPNSGDMIEFG  60
             MACKGFWECLLKLLNFLLTLVGLTMVGYGIYLFVEYKNHSHSGDDYPVAPPNSGDMIEFG
GNL_R  1     MACKGFWECLLKLLNFLLTLVGLTMVGYGIYLFVEYKNHSHSGDDYPVAPPNSGDMIEFG  60

SL3_00 61    RPMLMAVSLAENIFDKLPKPWFIYLFIGIGAVLVVVSCCGCIGAATRNGCCLSCYSMLIF  120
             RPMLMAVSLAENIFDKLPKPWFIYLFIGIGAVLVVVSCCGCIGA TRNGCCLSCYSMLIF
GNL_R  61    RPMLMAVSLAENIFDKLPKPWFIYLFIGIGAVLVVVSCCGCIGA-TRNGCCLSCYSMLIF  119

SL3_00 121   LLILVELGAAGFIFFDKSWKDEIPRDKTGNFETIYDFLDDHWKIIKWVALGAVIFEALIF  180
             LLILVELGAAGFIFFDKSWKDEIPRDKTGNFETIYDFLDDHWKIIKWVALGAVIFEALIF
GNL_R  120   LLILVELGAAGFIFFDKSWKDEIPRDKTGNFETIYDFLDDHWKIIKWVALGAVIFEALIF  179

SL3_00 181   LLALVVRAANRPADYDSDDEYIGGPRQQIRQPLINNRPPANPATGVPVTATLDNRPSRND  240
             LLALVV AANRPADYDSDDEYIGGPRQQIRQPLINNRPPANPAT VPVTATLDNRPSRND
GNL_R  180   LLALVVGAANRPADYDSDDEYIGGPRQQIRQPLINNRPPANPATSVPVTATLDNRPSRND  239

SL3_00 241   AWSTRMREKYGLDTSEPTYNPSESNRYPPTAAQPQSERKGCTIM  284
             AWSTRMREKYGLDTSEPTYNPSESNRYPPTAAQPQSERKGC IM
GNL_R  240   AWSTRMREKYGLDTSEPTYNPSESNRYPPTAAQPQSERKGCAIM  283
```

Figure 7 – qPCR results showing virus titer of material with the individual QTLs of chr 8 and 11, and the combination.

GENE LEADING TO ToBRFV RESISTANCE IN *S. lYCOPERSICUM*

RELATED APPLICATIONS AND INCORPORATION BY REFERENCE

This application is a continuation-in-part application of international patent application Serial No. PCT/EP2021/070104 filed 19 Jul. 2021, which published as PCT Publication No. WO 2022/013452 on 20 Jan. 2022, which claims benefit of international patent application Serial No. PCT/EP2020/070347 filed 17 Jul. 2020.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing, which has been submitted electronically and is hereby incorporated by reference in its entirety. Said XML copy, was created Jan. 2, 2023, is named Y7954_00561SL.xml and is 79,737 bytes in size.

FIELD OF THE INVENTION

The present invention relates to a tomato (*Solanum lycopersicum*) plant comprising a QTL which comprises an allele of a gene that leads to Tomato brown rugose fruit virus (ToBRFV) resistance. The present invention further relates to an allele of a gene that confers ToBRFV resistance, methods for producing a ToBRFV resistant *Solanum lycopersicum* plant, methods for identification and selection of such a plant comprising the allele of the gene, progeny, seed and fruit of the Tomato brown rugose fruit virus resistant *Solanum lycopersicum* plant, to propagation material suitable for producing the *Solanum lycopersicum* plant, and to a food product comprising such tomato fruit or part thereof, a cell or a tissue culture that results from or can be regenerated into a Tomato brown rugose fruit virus resistant *Solanum lycopersicum* plant and a marker for identification of the allele of the gene that leads to Tomato brown rugose fruit virus resistance in *Solanum lycopersicum*, and to use of said marker.

BACKGROUND OF THE INVENTION

Viral diseases pose one of the major threats vegetable growers have to deal with, both in protected and open field crop cultivation. Once a crop is infected, spread of the virus can occur rapidly through hard-to-control vectors, usually insects. In addition, cultivation methods often contribute to a further spread of the virus, by sap transmission through tools and fieldworkers.

The best protection against virus infection is the use of a resistant variety. Resistances against many known viruses have been identified, which resistances are incorporated in suitable tomato varieties through breeding, allowing the growers to obtain a good yield even under virus pressure. Resistances can usually be categorized into different types, the most common ones being tolerance and resistance. Tolerance does not necessarily mean the resistance has a lower level, but it indicates there are no or reduced symptoms in the plant, even though the virus can still replicate within the host. Resistance describes a mechanism in which not only symptoms are absent or strongly reduced, but also virus replication within the plant is restricted, i.e. it is absent or strongly reduced.

In 2015 the occurrence of a new tobamovirus in tomato was published (Salem et al: A new tobamovirus infecting tomato crops in Jordan. Arch Virol. 2016 February; 161(2): 503-6. Epub 2015 Nov. 19). This virus was shown to be related to the known tobamoviruses Tobacco mosaic virus (TMV), Tomato mosaic virus (ToMV), and Tomato mild mottle virus (ToMMV), with sequence identities of around 80% to 90% for the closest related sequences of ToMMV and ToMV. Symptoms were rather mild on the plant, but very severe brown rugose symptoms were present on almost all fruits. The virus was observed to break the resistance of the commonly used resistance genes against ToMV: Tm-1, Tm-2, and Tm-$2^2$, of which the latter one is also known as Tm-$2^a$. A later publication showed that the virus was also found in Israel, and it was established that the virus can also infect pepper (*Capsicum annuum*) plants (Luria et al (2017): A new Israeli tobamovirus isolate infects tomato plants harboring Tm-$2^2$ resistance genes. PLoS ONE 12(1): e0170429. Doi: 10.1371/journal.pone.0170429). Symptoms appeared to vary based on the affected variety, and in certain instances symptoms were mainly found on the vegetative parts in the form of severe or mild mosaic, necrosis, leaf distortion, or other symptoms. As the virus was clearly different from the known tobamoviruses it was assigned a new designation: Tomato brown rugose fruit virus (TBRFV). In the meantime, the commonly used abbreviation for this virus is ToBRFV, which is therefore now also used in the present application.

Over the past few years ToBRFV has quickly spread to many countries and has a major impact on tomato fruit production in a rapidly increasing number of areas of vegetable farming. Because of the severity of the symptoms on the fruits, the impact of the presence of ToBRFV for tomato growers is very high as it leaves the fruits basically unmarketable. The virus is at least transmitted mechanically, which makes the spread easy and rapid, and difficult to control. Transmission of the virus is also likely to occur through infected seed.

Citation or identification of any document in this application is not an admission that such document is available as prior art to the present invention.

SUMMARY OF THE INVENTION

It is an object of the present invention to provide a tomato plant of the species *Solanum lycopersicum* that shows true resistance to Tomato brown rugose fruit virus (ToBRFV).

It is a further object of the present invention to provide an allele of a gene that leads to ToBRFV resistance.

The present invention relates to a tomato (*Solanum lycopersicum*) plant comprising a QTL which comprises an allele of a gene that leads to Tomato brown rugose fruit virus (ToBRFV) resistance. The present invention further relates to an allele of a gene that confers ToBRFV resistance. The invention further relates to a method for producing a ToBRFV resistant *Solanum lycopersicum* plant, and methods for identification and selection of such a plant comprising the allele of the gene. The invention also relates to progeny, seed and fruit of the Tomato brown rugose fruit virus resistant *Solanum lycopersicum* plant, to propagation material suitable for producing the *Solanum lycopersicum* plant, and to a food product comprising such tomato fruit or part thereof. The invention further relates to a cell or a tissue culture that results from or can be regenerated into a Tomato brown rugose fruit virus resistant *Solanum lycopersicum* plant. The invention also relates to a marker for identification of the allele of the gene that leads to Tomato brown rugose fruit virus resistance in *Solanum lycopersicum*, and to use of said marker.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of tomato *Solanum lycopersicum* population 20R.1552Q08_04, comprising the resistance conferring Tom2a allele of the invention on chromosome 8 homozygously, were deposited with NCIMB Ltd, Ferguson Building, Craibstone Estate, Bucksburn, Aberdeen AB21 9YA, UK on 14 Jul. 2020 under deposit accession number NCIMB 43637.

The Deposit with NCIMB Ltd, under deposit accession number NCIMB 43637 was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIGS. 1A-1E—Nucleotide sequences of SEQ ID NOS: 1 to 44, including the SNP indicative for ToBRFV resistance.

FIGS. 5A-5C—CDS sequences Tom2a genes SEQ ID NO: 45: GNL_R (resistant), resistance conferring allele from GNL.3951, as present in NCIMB 43637; SEQ ID NO: 47: reference genome SL3_00 (susceptible); individually and alignment FIG. 6—Tom2a protein sequences SEQ ID NO: 46: protein encoded by resistance conferring Tom2a allele; SEQ ID NO: 48: wildtype protein, susceptible; encoded by reference sequence of SL3_00; individually and alignment FIG. 7—Average qPCR results showing virus titer (Cq_corr) of plants having the susceptible wildtype of a line used as susceptible parent in a cross developing isogenic lines, and plants of these isogenic lines having a QTL on chr 11, having the QTL that comprises the resistance conferring Tom2a allele of the present invention on chr 8, having the combination of QTLs on chr 8 and 11, and lacking both QTLs FIG. 8—Prediction of domains and membranes of the Tom2a protein

DETAILED DESCRIPTION OF THE INVENTION

Figure 2:
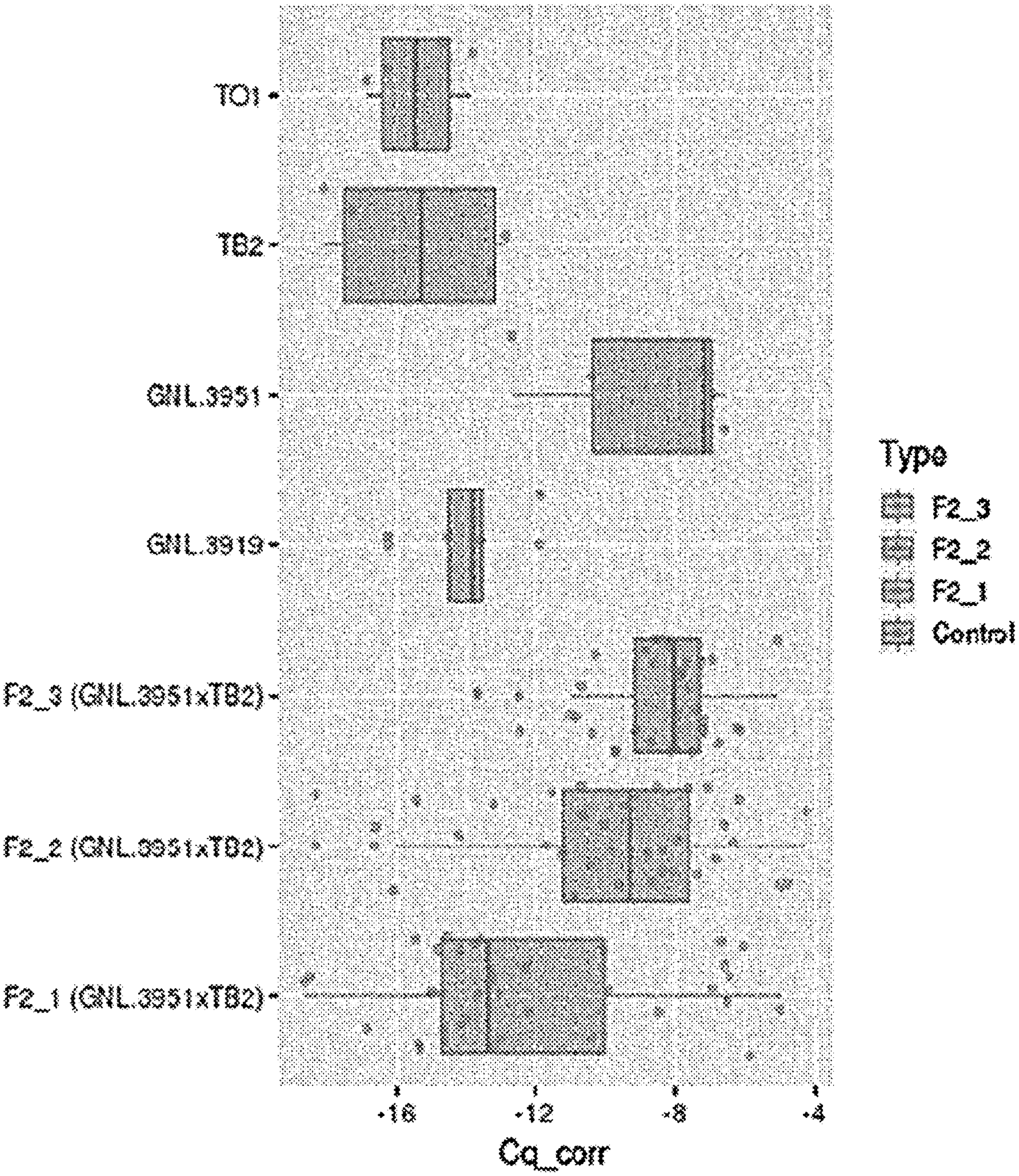
FIG. 2—variation in virus titer in susceptible lines, the resistant donor, and F2 populations based on qPCR observation FIG. 3—qPCR results of the deposits FIG. 4—identification of Tom2a as the causal gene for ToBRFV resistance, by marker analysis combined with phenotyping of recombinant lines.

Because the problems with the new ToBRFV spread very quickly and had a major effect on tomato production in certain areas, the urgency to obtain resistant tomato plants was very high. In addition, the virus was expected to be able to spread rapidly to other areas due to its very effective transmission. A large germplasm screen was therefore organized to get an insight in the presence of possible sources. Initially, several resistant accessions of the species *Solanum pimpinellifolium* were identified, and QTLs on chromosomes 6, 11, and 12 were found through fine mapplng and phenotyping of populations made between these sources and *S. lycopersicum* lines, as described in co-pending applications WO2019110130 and WO2019110821. Introgression of these QTLs into *S. lycopersicum* led to useful phenotypic resistance levels, but in lab experiments it was found that virus titer was still relatively high, which demonstrated that the virus could still replicate in the plant.

Therefore, for one of the used *S. pimpinellifolium* sources, GNL.3951, further populations were developed by combining it with internal breeding lines for additional QTL mapplng, to acquire plants with a more robust true resistance based on restriction of virus replication. On plants of all generations bio-assays were done, but also qPCR analysis was performed to determine the presence and level of virus titer in the plants (Example 2).

The identification and characterization of a QTL through molecular markers gives the opportunity to use genetically linked markers to identify the presence of the QTL and therefore the presence of the resistance, which is obviously much more efficient than the use of a bio-assay in combination with qPCR analysis. For this purpose, new QTL mapplng studies were performed on F2 populations, backcrosses, and F1 hybrids with the source. These observations resulted in the identification of a new QTL region on chromosome 8 (Example 1).

The present invention provides a *Solanum lycopersicum* plant that is resistant to Tomato brown rugose fruit virus (ToBRFV), which plant comprises a QTL comprising an allele of a gene on chromosome 8 that restricts virus replication in the plant. The allele of the gene on chromosome 8 is in particular an allele of a gene derived from or introgressed from the species *S. pimpinellifolium.*

The first QTL region that was identified on chromosome 8 was located between SEQ ID NO: 1 and SEQ ID NO: 42. The presence of this QTL on chromosome 8 can be identified by a genetically linked marker selected from the group consisting of the SNP presented in SEQ ID NOS: 1 to 42, preferably by a marker selected from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, and SEQ ID NO: 42. It was determined that the QTL was tightly linked to a marker selected from the group consisting of the SNP presented in SEQ ID NO: 26, SEQ ID NO: 29, and SEQ ID NO: 30. A genetically linked marker for identification of the QTL is a marker represented by any one of the sequences listed in FIG. 1 that is present in the QTL.

The initially identified QTL region on chromosome 8 was further finemapped to determine the position of the gene within the QTL that confers the resistance. A first finemapplng exercise resulted in a smaller QTL region, that was positioned between SEQ ID NO: 22 and SEQ ID NO: 34. This smaller QTL region comprised seven genes. Five markers from the first mapplng, including the three that were determined to be highly linked, were present in the sequence of one of those genes, the Tom2a gene, indicating the presence of polymorphisms in Tom2a as compared to the ToBRFV susceptible reference genome, version SL3_00. Because the best-linked markers were present in this gene, Tom2a appeared to be the most likely candidate gene for the ToBRFV resistance of the present invention. Sequencing of this gene, and subsequent alignment with the public reference genome, resulted in the determination of two more polymorphisms. The polymorphisms between the reference genome sequence SL3_00 and the resistant sequence of Tom2a can be identified by any one of the markers presented as SEQ ID NO: 26, SEQ ID NO: 27, SEQ ID NO: 28, SEQ ID NO: 29, SEQ ID NO: 30, SEQ ID NO: 43, or SEQ ID NO: 44. The resistant sequence of Tom2a constitutes the allele of the invention.

Further research and observations were done to confirm the involvement of the Tom2a gene in the ToBRFV resistance. In this process, populations that had recombinations in the QTL region were developed. Through marker analysis and phenotyping of these recombinant lines, the other genes that were present in the QTL region were eliminated as potential contributors to the ToBRFV resistance, and the Tom2a gene could be confirmed as the causal gene for the ToBRFV resistance of the present invention (Example 4; FIG. 4).

The invention relates to a *Solanum lycopersicum* plant comprising a QTL on chromosome 8 which comprises a resistance conferring Tom2a allele, wherein the presence of the QTL on chromosome 8 is genetically linked to at least one of the markers selected from the group consisting of the SNP presented in SEQ ID NOS: 1 to 44, preferably by a marker selected from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, SEQ ID NO: 42, SEQ ID NO: 43, and SEQ ID NO: 44, most preferably by a marker selected from the group consisting of SEQ ID NO: 26, SEQ ID NO: 27, SEQ ID NO: 28, SEQ ID NO: 29, SEQ ID NO: 30, SEQ ID NO: 43, and SEQ ID NO: 44.

The present invention provides a resistance conferring Tom2a allele on chromosome 8 of *Solanum lycopersicum*, which resistance conferring Tom2a allele comprises SEQ ID NO: 45, or comprises a homologous Tom2a sequence having at least 70% sequence identity to SEQ ID NO: 45. The presence of said resistance conferring Tom2a allele or homologous Tom2a sequence in a *S. lycopersicum* plant leads to ToBRFV resistance. SEQ ID NO: 45 presents the coding sequence (CDS) of a resistance conferring allele of Tom2a. As used herein, a resistance conferring allele of Tom2a is a version of the Tom2a gene that leads to ToBRFV resistance.

SEQ ID NO: 45 encodes a protein comprising SEQ ID NO: 46. The present invention relates to a Tom2a protein comprising SEQ ID NO: 46, or comprising a homologous Tom2a protein having at least 70% sequence identity to SEQ ID NO: 46, which leads to ToBRFV resistance.

The wildtype sequence of the Tom2a gene comprises SEQ ID NO: 47, and encodes a protein comprising SEQ ID NO: 48. Polymorphisms in the genomic sequence of this gene, which can be used to identify the presence of the resistance conferring allele of the Tom2a gene, comprise a SNP as presented in the sequences of SEQ ID NO: 26, SEQ ID NO: 27, SEQ ID NO: 28, SEQ ID NO: 29, SEQ ID NO: 30, SEQ ID NO: 43, or SEQ ID NO: 44. The resistance conferring allele of Tom2a can be identified by the use of any one of these SNPs as a marker, by determining the presence of the SNP.

A homologous Tom2a gene comprises a homologous sequence, which is a sequence having at least 70% sequence identity to SEQ ID NO: 45, preferably at least 75%, 77%, 80%, 83%, 85%, 87%, 90%, 93%, 95%, 96%, 97%, 98%, or 99% sequence identity. A homologous Tom2a protein comprises a homologous sequence, which is a sequence having at least 70% sequence identity to SEQ ID NO: 46, preferably at least 75%, 77%, 80%, 83%, 85%, 87%, 90%, 93%, 95%, 96%, 97%, 98%, or 99% sequence identity.

In one embodiment, a resistance conferring homologous Tom2a allele has retained a polymorphism that can be identified by SEQ ID NO: 26, or by SEQ ID NO: 28, or by SEQ ID NO: 43, or by SEQ ID NO: 44. In one embodiment, a resistance conferring Tom2a allele, or a homologous allele thereof, has retained a combination of polymorphisms that can be identified by SEQ ID NO: 26 and SEQ ID NO: 28; SEQ ID NO: 26 and SEQ ID NO: 43; SEQ ID NO: 26 and SEQ ID NO: 44; SEQ ID NO: 28 and SEQ ID NO: 43; SEQ ID NO: 28 and SEQ ID NO: 44; SEQ ID NO: 43 and SEQ ID NO: 44; SEQ ID NO: 26 and SEQ ID NO: 28 and SEQ ID NO: 43; SEQ ID NO: 26 and SEQ ID NO: 28 and SEQ ID NO: 44; SEQ ID NO: 26 and SEQ ID NO: 43 and SEQ ID NO: 44; SEQ ID NO: 28 and SEQ ID NO: 43 and SEQ ID NO: 44; or SEQ ID NO: 26 and SEQ ID NO: 28 and SEQ ID NO: 43 and SEQ ID NO: 44.

Because the gene is present on the minus-strand in the public genome, SEQ ID NO: 26 identifies an A to G conversion on position 559 of SEQ ID NO: 47; SEQ ID NO: 28 identifies a GGC deletion on positions 312-314 of SEQ ID NO: 47; SEQ ID NO: 43 identifies a G to A conversion on position 673 of SEQ ID NO: 47, and SEQ ID NO: 44 identifies an A to G conversion on position 844 of SEQ ID NO: 47.

In one embodiment, the resistance conferring homologous Tom2a allele has retained at least one of an A to G conversion on position 559 of SEQ ID NO: 47; a GGC deletion on positions 312-314 of SEQ ID NO: 47; a G to A conversion on position 673 of SEQ ID NO: 47, an A to G conversion on position 844 of SEQ ID NO: 47, or any of those polymorphisms on a corresponding position of the homologous Tom2a gene. In a further embodiment, the resistance conferring homologous Tom2a allele has retained a combination of two, three, or all four of these polymorphisms. FIG. 5 shows the CDS sequences of the Tom2a wildtype and the resistance conferring Tom2a allele individually and in an alignment.

In one embodiment, the homologous Tom2a allele sequence encodes a protein comprising at least one of a deletion of A on position 105 of SEQ ID NO: 48, a conversion to G on position 187 of SEQ ID NO: 48, a conversion to S on position 225 of SEQ ID NO: 48, or a conversion to A on position 282 of SEQ ID NO: 48.

In one embodiment, the protein encoded by the resistance conferring Tom2a allele, or a homologous protein thereof, has retained an Ala deletion on position 105 of SEQ ID NO: 48, a Arg to Gly substitution on position 187 of SEQ ID NO: 48, a Gly to Ser substitution on position 225 of SEQ ID NO: 48, or a Thr to Ala substitution on position 282 of SEQ ID NO: 48, or a modification on a corresponding position of an homologous protein. In one embodiment, the protein encoded by the resistance conferring Tom2a allele has retained a combination of two, three, or all four of these polymorphisms. FIG. 6 shows the Tom2a protein sequences of the wildtype and the resistance conferring Tom2a allele individually and in an alignment.

As used herein, sequence identity is the percentage of nucleotides or amino acids that is identical between two sequences after proper alignment of those sequences. The person skilled in the art is aware of how to align sequences, for example by using a sequence alignment tool such as BLAST®, which can be used for both nucleotide sequences and protein sequences. To obtain the most significant result, the best possible alignment that gives the highest sequence identity score should be obtained. The percentage sequence identity is calculated through comparison over the length of the shortest sequence in the assessment, whereby in the present case a sequence represents a gene that at least comprises a start codon and a stop codon, or a complete protein encoded by such a gene.

Figure 8:
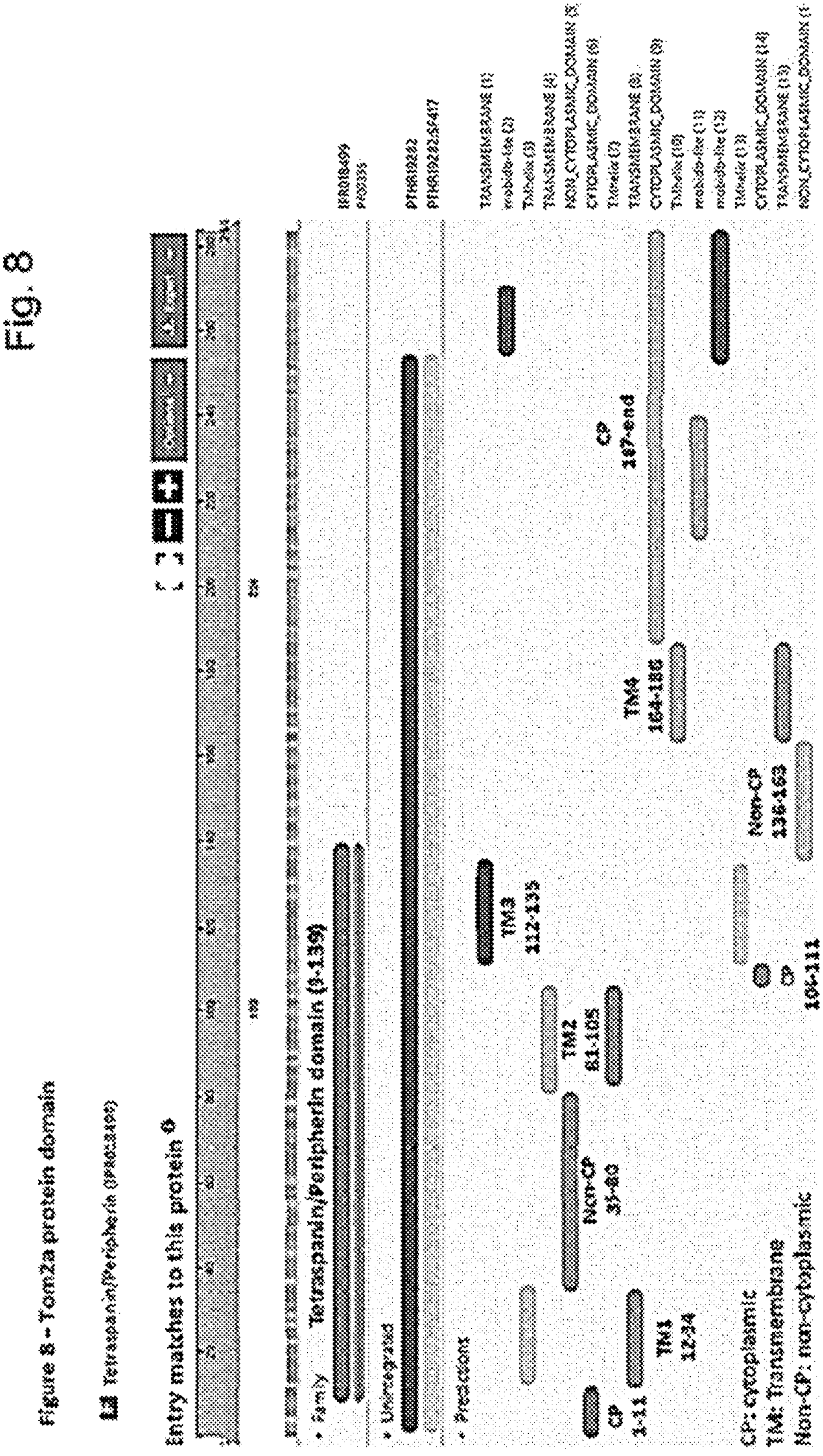

The Tom2a protein is a tetraspanin protein, which is a protein having a tetraspanin/peripherin domain. The protein comprises an N-terminal and a C-terminal tail, and four transmembrane domains which are connected by two non-cytoplasmic and one very short cytoplasmic loop (FIG. 8). The observed mutations were present at the end of the second transmembrane domain (TM2), which is in particular the Ala deletion of position 105, and in the C-terminal tail of the protein. The deletion of Ala on position 105 affects the TM2 domain, and might also have an effect on the short cytoplasmic loop that follows it. The present invention relates to a mutation in a Tom2a gene having an effect on the TM2 domain, or a mutation having an effect on the cytoplasmic loop, or a mutation having an effect on the C-terminal tail of the protein, or a combination of said mutations.

In one embodiment, the resistance conferring Tom2a allele encodes a non-functional protein.

FIG. 1 provides the sequences of the SEQ ID NOS: that can be used as markers, or used to develop markers, to identify the presence of the QTL comprising the allele of the Tom2a gene of the invention on chromosome 8 leading to ToBRFV resistance in a tomato plant. Table 4 shows the nucleotide in the sequence that identifies the presence of the QTL, and therefore a resistant plant, as well as the position of the SNP in the sequence of FIG. 1. As used herein, the 'SNP presented in' a certain SEQ ID NO:, is the nucleotide within the sequence that is indicative of resistance, as given in the column 'Nucleotide of the SNP in FIG. 1, to be used as marker of the invention' of Table 4. When the sequences of the markers are positioned on version SL3_00 of the publicly available genome reference sequence for *S. lycopersicum*, the physical position to which the SNP polymorphism in said marker sequence corresponds can be derived. This position is also presented in Table 4. Version SL3_00 of the public *S. lycopersicum* genome reference sequence can for example be accessed at the Solgenomics website (solgenomics.net) and is the reference for 'the public tomato genome' as used herein. The positions of the markers of the invention are derivable from a public map and these positions are relative to said physical positions.

Identifying the presence of the QTL, or of the resistance conferring Tom2a allele, by using a marker is in particular done by identifying the presence of the nucleotide at the position of the SNP within the marker sequence that is indicative for the resistance. The wildtype nucleotide is the nucleotide that is present on that position in the public genome.

As used herein, a tomato plant is a plant of the species *Solanum lycopersicum.*

As used herein, resistance to the Tomato brown rugose fruit virus is resistance to the virus as described in Salem et al (2016, supra), which virus was assigned NCBI Taxonomy ID 1761477.

As used herein, a marker is genetically linked to, and can therefore be used for the identification of, the QTL which comprises the allele of the Tom2a gene of the invention, when the marker and the ToBRFV resistance co-segregate in a segregating population resulting from a cross between a plant comprising the QTL of the invention and a plant lacking the QTL. A marker that is genetically linked to a QTL can be used for identification of that QTL because a linked marker is present in said QTL. Markers that are present in the resistance conferring Tom2a allele of the invention are completely linked, and are therefore directly indicative of the presence of the resistance conferring allele of the gene.

The ToBRFV resistance of the present invention inherits in a recessive manner. This means that when the allele of the Tom2a gene of the invention is homozygously present, virus replication in the plant is absent or strongly reduced, when compared to a plant in which the allele of the invention is absent or heterozygously present. However, heterozygous plants can be used for development of homozygous plants through crossing and selection, and heterozygous plants therefore also form a part of this invention.

Virus replication, and thereby the ToBRFV resistance of the invention, is suitably determined through a qPCR test, as described in Example 2. Confirmation of the resistance can be determined through a bioassay, for example using a standard sap-mechanical inoculation technique for tobamoviruses, which is known to the skilled person, and is also for example described in Luria et al (2017, supra).

To determine resistance phenotypically, seeds of the accessions to be tested are sown in standard seedling trays and at least 10 seedlings are inoculated 4 weeks after sowing. Inoculum is prepared by grounding leaves of tomato plants that were infected with ToBRFV in a 0.01 M phosphate buffer (pH 7.0) mixed with celite. The seedlings are then dusted with carborundum powder prior to gently rubbing the leaf with inoculum. Resistance is scored on a scale of 0-5; the description of the scales of the scores can be found in Table 3. Observation of the symptoms on the young tomato plants in the bio-assay is done 14-21 days after inoculation (dai).

ToBRFV resistance is determined by comparison to a control variety known to be ToBRFV susceptible. Examples of ToBRFV susceptible tomato varieties that do not have the resistance conferring Tom2a allele of the invention on chromosome 8, to be used as susceptible control, are Livento F1 and Adventure F1. Since no tomato varieties with the ToBRFV resistance of the invention were known before the invention was done, it was not possible to include a resistant control that was known before the present invention was done. However, as a resistant control a plant grown from seed deposited as NCIMB 43637 can be used; a plant grown from this deposit comprises the resistance conferring Tom2a allele of the invention on chromosome 8. The test is performed with 10 plants of a certain line, and the average score is taken. The test is performed properly when susceptible (S) controls have an average score that is higher than 3.0, preferably higher than 3.5. Once this average is reached is a correct moment to score the assay.

TABLE 3 scales ToBRFV resistance scores

| Score | Symptoms |
|---|---|
| 0 | No symptoms |
| 1 | Not clean, a single spot, some minor discoloration |
| 2 | Mosaic, clear visible symptoms |
| 3 | Severe mosaic, starting deformation in the head |
| 4 | Severe mosaic, necrosis on the stem, serious deformation in the head, spots in blisters |
| 5 | Dead plant |

As used herein, a ToBRFV resistant tomato plant homozygously comprising the resistance conferring Tom2a allele of the invention on chromosome 8 has an average score of 1.5 or lower than 1.5, preferably a score lower than 1.0, when scoring according to Table 3 is used.

As used herein, resistance means that replication of the virus is reduced or absent in a plant that is infected with ToBRFV. Reduction of virus replication can be measured by a qPCR test. To determine if a line has reduction or absence of ToBRFV virus replication, the virus titer is determined in leaf samples which are taken from at least 5 plants of that line that are ToBRFV infected. From each plant a leaf punch of 6 mm in diameter is taken and subsequently ground in 500 μl of PBS buffer solution. 50 μl of the resulting suspension is used in a 96-well KingFisher Flex isolation protocol, whereby isolation of the leaf material is done using the innuPREP DNA/RNA virus PLUS Kit. The samples are then analysed in a 96CFX qPCR thermocycler (Biorad) to get a Cq_ToBRFV value, which represents the number of cycles needed to obtain the virus PCR product, using a programme of 5 minutes on 50° C. and 20 sec. on 95° C., followed by 40 cycles of 10 sec. on 95° C. and 60 sec. on 60° C.

To be able to compare the values of samples of different sizes and backgrounds, the *S. lycopersicum* PHD reference gene, a tomato housekeeping gene, is included in the qPCR assay, which corrects any variation in the amount of sample material, and then yields a Cq_PHD value. The primers used in the assay are given in Table 1. The PCR volumes that are used in the assay are given in Table 2.

TABLE 1

ToBRFV and PHD primers for qPCR assay

| Primers | Sequence |
|---|---|
| TBFRV FW 3 (SEQ ID NO: 49) | GTACATCTTGCTGGTCTTGT |
| TBFRV RV 3 (SEQ ID NO: 50) | CGCTCTCTCCATTCTCTTATC |
| TBFRV P3 (SEQ ID NO: 51) | FAM-TGGTGGTGTCAGTGTCT GTTTGGT-BHQ1 |
| PHD FW1 (SEQ ID NO: 52) | TACCAACTCTTCCTCCCATAG |
| PHD RV1 (SEQ ID NO: 53) | TGGATCGCACTGTGAGTA |
| PHD P1 (SEQ ID NO: 54) | TxR 5'-TTCAAAGACTTC TCCGCCCGTCAC-3' BHQ2 |

TABLE 2 qPCR assay volumes

| PCR-volumes | 1× (μl) |
|---|---|
| 4× TaqMan fast virus1-step (Applied Biosystems) | 6.25 |
| TBRFV FW3 (20 pmol/μl) | 0.30 |
| TBRFV RV3 (20 pmol/μl) | 0.30 |
| TBRFV P3 (20 pmol/μl) | 0.20 |
| PHD FW1 (20 pmol/μl) | 0.30 |
| PHD RV1 (20 pmol/μl) | 0.30 |
| PHD P1 (20 pmol/μl) | 0.20 |
| Milli Q | 15.15 |
| RNA | 2.00 |
| Total volume | 25 |

To accurately determine the final value for virus titer the delta-delta Ct method is used, with PHD as a housekeeping gene and ToBRFV as the gene of interest. The final value is the Cq_corr, which is calculated as Cq_ToBRFV−Cq_PHD. A plant is determined to have a reduction of ToBRFV virus replication when the average Cq_corr of at least 5 plant samples is higher than −11.00, or when the average Cq-corr is at least 5.00 higher than the average Cq_corr of a susceptible control (Example 2, Table 5).

In one embodiment a resistant plant of the invention that comprises the resistance conferring Tom2a allele of the invention on chromosome 8 as defined herein has an average Cq_corr score that is in order of increased preference higher than −11.00 −10.50, −10.00, −9.50, −9.00, −8.50, −8.00, −7.50, or −7.00.

In one embodiment a resistant plant of the invention that comprises the resistance conferring Tom2a allele of the invention on chromosome 8 as defined herein has an average Cq_corr score that is in order of increased preference at least 5.00, 5.50, 6.00, 6.50, 7.00, 7.50, 8.00 higher than the average value of a susceptible control.

Calculation of an average value as described above is preferably done as an average taken of at least 2 trials. Plants are properly infected with ToBRFV when the susceptible control in a test has an average Cq_corr value of −12 or lower, preferably −13 or lower, most preferably −14 or lower.

A *S. lycopersicum* plant that has the resistance conferring Tom2a allele of the invention that leads to ToBRFV resistance can be grown from seed deposited as NCIMB 43637.

NCIMB 43637 has the ToBRFV resistance of the invention and comprises the QTL of the invention on chromosome 8 that is located between SEQ ID NOS: 1 and 42, which comprises the resistance conferring Tom2a allele having SEQ ID NO: 45. The QTL, and thereby the resistance conferring Tom2a allele, is present in deposit NCIMB 43637 in homozygous form. The QTL in NCIMB 43637 is linked to any of the markers represented by the SNP presented in SEQ ID NOS: 1 to 44, and can therefore be identified by any one of the markers represented by the SNP presented in SEQ ID NOS: 1 to 44. The resistance conferring Tom2a allele in NCIMB 43637 comprises the polymorphisms presented in SEQ ID NO: 26, SEQ ID NO: 27, SEQ ID NO: 28, SEQ ID NO: 29, SEQ ID NO: 30, SEQ ID No, 43, and SEQ ID NO: 44. A resistance conferring Tom2a allele can in particular be identified by determining the presence of a SNP presented in SEQ ID NO: 26, SEQ ID NO: 28, SEQ ID NO: 43, or SEQ ID NO: 44.

A plant comprising the resistance conferring Tom2a allele of the invention on chromosome 8 can be used as a resistant control variety in a ToBRFV bio-assay or qPCR test. When a plant, line, or population to be assessed shows the same resistance as NCIMB 43637, and this plant, line or population comprises the resistance conferring Tom2a alleleas described herein on chromosome 8, this plant, line, or population is considered to have the ToBRFV resistance of the invention and is therefore a plant of the invention.

A plant of the present invention is optionally a cultivated *S. lycopersicum* plant having improved agronomic characteristics that make it suitable for commercial cultivation. The plant is thus an agronomically elite plant.

In one embodiment, a ToBRFV resistant *S. lycopersicum* plant of the present invention does not require a resistance conferring allele of the Tm-1 gene. In one embodiment, a ToBRFV resistant *S. lycopersicum* plant of the present invention does not require a resistance conferring TOM1 gene or TOM3 gene. A ToBRFV resistant *S. lycopersicum* plant of the invention comprising a resistance conferring Tom2a allele does not require the presence of a tobamo-resistance-conferring Tm-1 gene, TOM1 gene, or TOM3 gene to show resistance.

In one embodiment, a ToBRFV resistant *S. lycopersicum* plant of the present invention comprises a resistance conferring Tom2a allele and a resistance conferring QTL on chromosome 11, as described in co-pending application WO2019110821. Said resistance conferring QTL on chromosome 11 in particular comprises a resistance conferring CCA gene or a resistance conferring Albino3-like gene as described in WO2021110855 and co-pending application PCT/EP2021/055008, respectively. The combination of these QTLs, in particular of a resistance conferring Tom2a allele with either of said genes, results in a stronger and more durable ToBRFV resistance in *S. lycopersicum.*

The invention also relates to a tomato fruit harvested from a plant of the invention, wherein the tomato fruit comprises the resistance conferring Tom2a allele of the invention in its genome, which leads to ToBRFV resistance in the plant. This tomato fruit is also referred to herein as 'the fruit of the invention' or 'the tomato fruit of the invention'. As used herein, a 'tomato fruit' is a fruit produced by a plant of the species *Solanum lycopersicum.*

The present invention relates to a method for producing a ToBRFV resistant *S. lycopersicum* plant comprising introducing a QTL comprising a resistance conferring Tom2a allele on chromosome 8 in a *S. lycopersicum* plant lacking said QTL, wherein the QTL region is located between SEQ ID NO: 1 and SEQ ID NO: 42, and is linked to any of the markers selected from the group consisting of the SNP presented in SEQ ID NOS: 1 to 44, preferably to a marker selected from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, SEQ ID NO: 42, SEQ ID NO: 43, and SEQ ID NO: 44, most preferably by a marker selected from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44.

The present invention relates to a method for producing a ToBRFV resistant *S. lycopersicum* plant comprising introducing a resistance conferring Tom2a allele as described herein in a *S. lycopersicum* plant lacking said allele.

The resistance conferring Tom2a allele of the invention can be introduced from another plant, which comprises the resistance conferring Tom2a allele, through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cis-genesis can be applied. Suitably markers as described herein are used to follow the incorporation of the resistance conferring Tom2a allele into another plant.

The above method can in particular be used to introduce the resistance conferring Tom2a allele of the invention into a plant species that is suitable for incorporation of such genetic information. In a particular embodiment, said resistance conferring Tom2a allele can be introduced from a *Solanum pimpinellifolium* plant comprising the resistance conferring Tom2a allele, or from another *Solanum* species that is sexually compatible to *S. lycopersicum*, into a *Solanum lycopersicum* plant lacking the resistance conferring Tom2a allele, for example by using standard breeding methods comprising crossing and selection. In another embodiment said resistance conferring Tom2a allele can be introduced from a *Solanum lycopersicum* plant comprising the resistance conferring Tom2a allele into a *Solanum lycopersicum* plant lacking the resistance conferring Tom2a allele using standard breeding methods.

The resistance conferring Tom2a allele on chromosome 8 can be introduced from a *Solanum lycopersicum* plant representative seed of which was deposited with the NCIMB under deposit number NCIMB 43637, or from the deposited seed of NCIMB 43637, or from progeny of the deposit, which are sexual or vegetative descendants thereof. Introduction of the resistance conferring Tom2a allele on chromosome 8 in *Solanum lycopersicum* leads to ToBRFV resistance.

Alternatively, the resistance conferring Tom2a allele of the invention can be transferred or introduced from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention, for example by editing an endogenous susceptible Tom2a gene to modify it into a resistance conferring Tom2a allele. A susceptible Tom2a gene can in particular be targeted to induce a mutation resulting in a deletion of Ala on position 105 of SEQ ID NO: 48, a conversion of Arg to Gly on position 187 of SEQ ID NO: 48, a conversion of Gly to Serine on position 225 of SEQ ID NO: 48, or a conversion of Thr to Ala on position 282 of SEQ ID NO: 48, or any of those modifications on a corresponding position of a homologous protein. A targeted modification resulting in a combination of those modifications also forms part of the invention. A susceptible Tom2a gene can further be edited to obtain a non-functional Tom2a protein, which is part of the invention.

The invention further relates to a plant of the invention comprising the resistance conferring Tom2a allele of the invention leading to ToBRFV resistance either homozygously or heterozygously. The plant is a plant of an inbred line, a hybrid, a doubled haploid, or a plant of a segregating population. Preferably, the plant of the invention is a non-transgenic plant.

The invention also relates to a *Solanum lycopersicum* seed comprising the resistance conferring Tom2a allele of the invention on chromosome 8, wherein the plant grown from the seed is a plant of the invention. In a preferred embodiment, the resistance conferring Tom2a allele of the invention is homozygously present in the seed and the plant grown from the seed is resistant to ToBRFV. The invention also relates to seed produced by a plant of the invention wherein the seed harbors the resistance conferring Tom2a allele of the invention, and as such, a plant grown from said seed is a plant of the invention. The invention also relates to use of said seed for the production of a plant of the invention, by growing said seed into a plant. The invention also relates to a plant part of a plant of the invention, which comprises a fruit or a seed, wherein the plant part comprises the resistance conferring Tom2a allele of the invention on chromosome 8 in its genome.

Moreover, the invention also relates to a food product or a processed food product comprising the tomato fruit of the invention or part thereof. The food product may have undergone one or more processing steps. Such a processing step might comprise but is not limited to any one of the following treatments or combinations thereof: peeling, cutting, washing, juicing, cooking, cooling or a salad mixture comprising the fruit of the invention. The processed form that is obtained is also part of this invention.

The invention also relates to propagation material suitable for producing a *Solanum lycopersicum* plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, and a stem; wherein the plant produced from the propagation material comprises the resistance conferring Tom2a allele of the invention on chromosome 8 as defined herein that confers ToBRFV resistance. A plant of the invention may be used as a source of the propagation material.

The invention further relates to a cell comprising the resistance conferring Tom2a allele of the invention as defined herein. A cell of the invention can be obtained from, or be present in, a plant of the invention. Such a cell may either be in isolated form, or a part of a complete plant, or from a part thereof, and still constitutes a cell of the invention because such a cell comprises the genetic information that determines the resistance conferring Tom2a allele as described herein that leads to ToBRFV resistance of a cultivated *S. lycopersicum* plant. Each cell of a plant of the invention carries the genetic information that leads to ToBRFV resistance. A cell of the invention may also be a regenerable cell that can regenerate into a new plant of the invention. The presence of the genetic information in this context is the presence of the resistance conferring Tom2a allele of the invention on chromosome 8, wherein the resistance conferring Tom2a allele is as defined herein.

The invention further relates to plant tissue of a plant of the invention, which comprises the resistance conferring Tom2a allele of the invention on chromosome 8 as defined herein. The tissue can be undifferentiated tissue or already differentiated tissue. Undifferentiated tissue is for example a stem tip, an anther, a petal, or pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny comprises the resistance conferring Tom2a allele of the invention on chromosome 8 as defined herein, the presence of which resistance conferring Tom2a allele, preferably in homozygous form, leads to ToBRFV resistance. Such progeny can in itself be a plant, a cutting, a seed, a cell, or a tissue.

As used herein, 'progeny' is intended to mean the first and all further descendants, such as an F1, F2, or further generation, from a cross with a plant of the invention, wherein a cross comprises a cross with itself or a cross with another plant, and wherein a descendant that is determined to be progeny comprises the resistance conferring Tom2a allele of the invention on chromosome 8 as defined herein that leads to resistance to ToBRFV. The plant of the invention that is used in this cross is optionally a plant grown from seed of deposit NCIMB 43637, or from progeny seed thereof which is a direct or further descendant through crossing a plant grown from the deposited seed with itself or with another plant for one or more subsequent generations, wherein the progeny seed has retained the resistance conferring Tom2a allele of the invention on chromosome 8.

Progeny also encompasses a *S. lycopersicum* plant that carries the resistance conferring Tom2a allele of the invention on chromosome 8 and is resistant to ToBRFV, and is obtained from the plant, or progeny of a plant, of the invention by vegetative propagation or another form of multiplication.

The invention further relates to a part of a *S. lycopersicum* plant of the invention that is suitable for sexual reproduction, which plant part comprises the resistance conferring Tom2a allele of the invention on chromosome 8, which resistance conferring Tom2a allele is as defined herein. Such a part is for example selected from the group consisting of a microspore, a pollen, an ovary, an ovule, an embryo sac, and an egg cell.

Additionally, the invention relates to a part of a *S. lycopersicum* plant of the invention that is suitable for vegetative reproduction, which is in particular a cutting, a root, a stem, a cell, or a protoplast that comprises the resistance conferring Tom2a allele of the invention on chromosome 8, which resistance conferring Tom2a allele is as defined herein. A part of a plant as previously mentioned is considered propagation material. The plant that is produced from the propagation material comprises the resistance conferring Tom2a allele of the invention on chromosome 8 as defined herein, the presence of which resistance conferring Tom2a allele leads to ToBRFV resistance.

The invention further relates to tissue culture of a plant of the invention, which is also propagation material and which comprises the resistance conferring Tom2a allele of the invention on chromosome 8 in its genome, which resistance conferring Tom2a allele is as defined herein. The tissue culture comprises regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, or a stem. The tissue culture can be regenerated into a *S. lycopersicum* plant comprising the resistance conferring Tom2a allele of the invention on chromosome 8 as defined herein, wherein the regenerated *S. lycopersicum* plant expresses ToBRFV resistance and is also part of the invention.

The invention additionally relates to the use of a plant of the invention in plant breeding. The invention thus also relates to a breeding method for the development of a cultivated *S. lycopersicum* plant that is resistant to ToBRFV, wherein a plant comprising the resistance conferring Tom2a allele of the invention on chromosome 8 as defined herein is used for conferring said resistance to another plant. Seed being representative of a plant that can be used in plant breeding to develop another plant with ToBRFV resistance was deposited with the NCIMB under accession number NCIMB 43637.

The invention also relates to the use of the QTL of the invention on chromosome 8, in particular to the use of a resistance conferring Tom2a allele as defined herein, for the development of a *Solanum lycopersicum* plant that has resistance to ToBRFV.

The invention also relates to a marker for the identification of ToBRFV resistance in a *Solanum lycopersicum* plant, or in a *Solanum pimpinellifolium* plant, or in a plant of another *Solanum* species that is sexually compatible with *Solanum lycopersicum*, which marker is selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44. Any other marker that is developed based on a polymorphism in the region defined above between SEQ ID NO: 1 and SEQ ID NO: 42, in particular based on a polymorphism compared to SEQ ID NO: 47, is also part of the invention.

The use of any of the markers from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44, for identification of ToBRFV resistance in a *Solanum lycopersicum* plant, or in a *Solanum pimpinellifolium* plant, or in a plant of another *Solanum* species that is sexually compatible with *Solanum lycopersicum*, is also part of the invention. Any use of these markers to develop other markers for the identification of the QTL on chromosome 8, in particular for the identification of a resistance conferring Tom2a allele leading to ToBRFV resistance, comprising determining any other polymorphism in the region between SEQ ID NOS: 22 and 34, is also part of the present invention.

The present invention also relates to a method for selecting a ToBRFV resistant *Solanum lycopersicum* plant, or a ToBRFV resistant *Solanum pimpinellifolium* plant, or a plant of another *Solanum* species that is sexually compatible with *Solanum lycopersicum* that is ToBRFV resistant, comprising identifying the presence of the resistance conferring Tom2a allele of the invention on chromosome 8, and selecting a plant that comprises said resistance conferring Tom2a allele as a ToBRFV resistant plant.

Identifying the presence of the resistance conferring Tom2a allele of the invention on chromosome 8 is suitably done using at least one of the markers selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44.

The invention also relates to a method of testing a *Solanum lycopersicum* plant, a *Solanum pimpinellifolium* plant, or a plant of another *Solanum* species that is sexually compatible with *Solanum lycopersicum*, for the presence of the resistance conferring Tom2a allele of the invention that confers ToBRFV resistance, comprising detecting the presence of a marker sequence selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44, in the genome of the plant.

The method of testing a *Solanum lycopersicum* plant, a *Solanum pimpinellifolium* plant, or a plant of another *Solanum* species that is sexually compatible with *Solanum lycopersicum*, for the presence of the resistance conferring Tom2a allele of the invention that confers ToBRFV resistance optionally further comprises selecting a *Solanum lycopersicum* plant, a *Solanum pimpinellifolium* plant, or a plant of another *Solanum* species that is sexually compatible with *Solanum lycopersicum*, that comprises said resistance conferring Tom2a allele as a ToBRFV resistant plant. The *Solanum lycopersicum* plant, *Solanum pimpinellifolium* plant, or a plant of another *Solanum* species that is sexually compatible with *Solanum lycopersicum*, that is thus selected can subsequently be used as a source for introgressing the ToBRFV resistance conferring Tom2a allele into a *S. lycopersicum* plant lacking the resistance conferring Tom2a allele.

The invention also relates to a method for the production of a *Solanum lycopersicum* plant which is resistant to ToBRFV, said method comprising:

a) crossing a plant of the invention, which comprises the resistance conferring Tom2a allele of the invention on chromosome 8, with another plant;
b) optionally performing one or more rounds of selfing and/or crossing of the plant resulting from the cross to obtain a further generation population;

c) selecting from the population resulting from the cross of step a), or from the further generation population of step b), a plant that comprises the resistance conferring Tom2a allele on chromosome 8 as defined herein, which plant is resistant against ToBRFV when the resistance conferring Tom2a allele is homozygously present.

The invention also relates to a method for the production of a *Solanum lycopersicum* plant which is resistant to ToBRFV, said method comprising:

a) crossing a first parent plant comprising the resistance conferring Tom2a allele of the invention on chromosome 8 with a second parent plant, which is a plant not comprising the resistance conferring Tom2a allele of the invention;
b) backcrossing the plant resulting from step a) with the second parent plant for at least three generations;
c) selecting from the third or higher backcross population a plant that comprises at least the resistance conferring Tom2a allele on chromosome 8 of the first parent plant of step a).

Selection of a plant comprising the resistance conferring Tom2a allele on chromosome 8 is suitably done by using a molecular marker genetically linked to the resistance conferring Tom2a allele, which marker is selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44, for the identification of the resistance conferring Tom2a allele on chromosome 8. The plant can alternatively, or in addition, be confirmed to have resistance to ToBRFV, in particular by performing a qPCR test for determining the absence or strong reduction of virus titer in the plant after ToBRFV infection.

In one embodiment, the plant of the invention used in the method for the production of a *Solanum lycopersicum* plant which is resistant against ToBRFV is a plant grown from seed deposited under NCIMB accession numbers NCIMB 43637, or a progeny plant thereof.

The invention additionally provides for a method of introducing another desired trait into a *Solanum lycopersicum* plant comprising ToBRFV resistance, comprising:

a) crossing a *Solanum lycopersicum* plant of the invention comprising the resistance conferring Tom2a allele on chromosome 8 with a second *Solanum lycopersicum* plant that comprises the other desired trait to produce F1 progeny;
b) optionally selecting in the F1 for a plant that comprises the resistance conferring Tom2a allele and the other desired trait;
c) crossing the optionally selected F1 progeny with either parent, to produce backcross progeny;
d) selecting backcross progeny comprising ToBRFV resistance and the other desired trait; and
e) optionally repeating steps c) and d) one or more times in succession to produce selected fourth or higher backcross progeny that comprises the other desired trait and has resistance to ToBRFV. Backcrossing is optionally done until the backcross progeny is stable and can be used as a parent line, which can be reached after 3 up to 10 backcrosses.

In one embodiment, the plant of the invention used in the method of introducing another desired trait into a *Solanum lycopersicum* plant comprising resistance to ToBRFV is a plant grown from seed deposited under NCIMB accession number NCIMB 43637, or a progeny plant thereof.

Optionally, selfing steps are performed after any of the crossing or backcrossing steps in above described methods. Selection of a plant comprising the resistance conferring Tom2a allele of the invention on chromosome 8 that leads to ToBRFV resistance and the other desired trait can alternatively be done following any crossing or selfing step of the method. The other desired trait can be selected from, but is not limited to, the following group: resistance to bacterial, fungal or viral diseases, insect or pest resistance, improved germination, plant size, plant type, improved yield, improved shelf-life, tolerance to water stress, tolerance to salt stress, tolerance to heat stress, and male sterility. The invention includes a *Solanum lycopersicum* plant produced by this method and a tomato fruit obtained therefrom.

The invention further relates to a method for the production of a *Solanum lycopersicum* plant comprising the resistance conferring Tom2a allele of the invention on chromosome 8, wherein the homozygous presence of the resistance conferring Tom2a allele leads to resistance to ToBRFV, by using tissue culture or by using vegetative propagation.

The invention further provides a method for the production of a *Solanum lycopersicum* plant comprising the resistance conferring Tom2a allele of the invention on chromosome 8 and having resistance to ToBRFV as defined herein by using a doubled haploid generation technique to generate a doubled haploid line that homozygously comprises the resistance conferring Tom2a allele of the invention and is resistant against ToBRFV.

The invention further relates to a method for the production of a *Solanum lycopersicum* plant comprising the resistance conferring Tom2a allele of the invention on chromosome 8 as defined herein, wherein the presence of said resistance conferring Tom2a allele leads to ToBRFV resistance, which method comprises growing a seed comprising said resistance conferring Tom2a allele into the said *Solanum lycopersicum* plant. In one embodiment, the seed used in the method is seed deposited with the NCIMB under deposit number NCIMB 43637, or progeny seed thereof.

The invention further relates to a method for seed production comprising growing a *Solanum lycopersicum* plant from a seed of the invention, allowing the plant to produce a tomato fruit with seed, harvesting the tomato fruit, and extracting those seed. Production of the seed is suitably done by crossing with itself or with another plant that is optionally also a plant of the invention. The seed that is so produced has the capability to grow into a plant that comprises the resistance conferring Tom2a allele of the invention. In a preferred embodiment in the plants used in seed production the resistance conferring Tom2a allele is homozygously present.

The invention further relates to hybrid seed and to a method for producing said hybrid seed, comprising crossing a first parent plant with a second parent plant and harvesting the resultant hybrid seed, wherein the first parent plant and/or the second parent plant are a plant of the invention comprising the resistance conferring Tom2a allele of the invention on chromosome 8 as defined herein. The resulting hybrid seed and the hybrid plant that can be grown from the hybrid seed is also a part of the invention. In a preferred embodiment both parents plants comprise the resistance conferring Tom2a allele of the invention and the hybrid seed comprises the resistance conferring Tom2a allele of the invention homozygously.

Introgression of the resistance conferring Tom2a allele of the invention on chromosome 8 as used herein comprises introduction of the resistance conferring Tom2a allele from a donor plant comprising said resistance conferring Tom2a allele into a recipient plant not carrying said resistance conferring Tom2a allele, or carrying the resistance conferring Tom2a allele heterozygously, by standard breeding techniques. Breeding methods such as crossing and selection, backcrossing, recombinant selection, or other breeding methods that result in the transfer of a genetic sequence from a resistant plant to a susceptible plant can be used. Selection for plants comprising the resistance conferring Tom2a allele of the invention can be performed by doing a qPCR test, or by doing a bio-assay by means of observation of the resistance to ToBRFV, or selection can be performed with the use of markers as defined herein, preferably a marker selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44, through marker assisted breeding, or combinations of these selection methods. The donor plant can be a *Solanum lycopersicum* plant, a *Solanum pimpinellifolium* plant, or a plant of another *Solanum* species that is sexually compatible with *S. lycopersicum*. Selection is started in the F1 or any further generation from an initial cross between the recipient plant and the donor plant, followed by either further crossing with itself or with another plant, suitably by using markers as identified and defined herein.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Mapplng of the ToBRFV Resistance QTL on Chromosome 8

It was observed that BC3F2 populations that were earlier made with *S. pimpinellifolium* source GNL.3951 and an internal breeding line TB2 had a good phenotypic resistance level, but they were segregating for virus titer level when a qPCR was done. The source itself had a low virus titer after infection (Example 2, FIG. 2, Table 5), so apparently not the complete resistance mechanism was transferred during the breeding process. Since the resistance was expected to be more reliable when virus replication is restricted, it was decided to cross the BC3F2 again with the donor plant to obtain a new F1. Subsequently F2 populations were made from 3 F1 plants, and again a qPCR observation was done to determine virus titer in the plants after infection with ToBRFV. Two of the populations were observed to have a virus titer level comparable to the source, which meant the plants did not only have no symptoms, but also virus replication in the plant was strongly reduced. However, the third population showed a lot of segregation in the qPCR test (Example 3, FIG. 2).

This observation was followed up with an extensive marker analysis to determine which genetic regions were still heterozygous, and to identify differences between the three populations. Through this, it appeared that a region on chromosome 8 might be responsible for the restriction in virus replication, and the better resistance level. This region was fixed for the two F2 populations that showed low virus titer, but was still segregating for the population that segregated for virus presence in the plant after infection. Through further fine-mapplng, this QTL region on chromosome 8 could be further narrowed down. Identification of recombinants within the original QTL initially resulted in a smaller region of approximately 1.5 Mbp, located between SEQ ID NO: 1 and SEQ ID NO: 42. Within this region, a number of polymorphic SNP markers that were linked to the QTL were identified.

Polymorphic SNP markers that were identified in this analysis and that are present in the QTL region are presented in Table 4. The exact physical positions of the SNPs as based on the public SL3_00 tomato map can also be found in Table 4. The sequences of these markers, i.e. the SNP that indicates resistance combined with a number of surrounding nucleotides to be used in marker design, are given in FIG. 1. These markers, in particular the SNPs in these markers, were determined to co-segregate with the QTL. The markers can be used to identify the presence of the QTL in plants grown from the deposits or in progeny thereof. These markers can further be used to identify the presence of the QTL of the invention for ToBRFV resistance on chromosome 8 in any other *S. lycopersicum* population that comprises the QTL. In addition, the markers can be used to identify resistance in *S. pimpinellifolium* or another *Solanum* species.

Further observations were done on F2 and F3 plants that were selected to have the QTL homozygously, which confirmed that the presence of the QTL resulted in a disease score averaging 0-1, occasionally towards 1.5, according to the scale described in Table 3, and a low virus titer when observed through a qPCR analysis. Further backcrosses were made with the breeding lines as recurrent parents, and also in subsequent selfed populations of the backcross generations the homozygous presence of the QTL was found to result in plants that were resistant to ToBRFV.

TABLE 4

SNP markers-nucleotides and physical positions

| Marker sequence (FIG. 1) | Nucleotide(s) of the SNP in FIG. 1, to be used as marker of the invention | Nucleotide(s) of the SNP in the wildtype (susceptible allele) | physical position of the SNP on the public SL3_00 genome map (wildtype) (in bp) | Type of polymorphism [wildtype/resistance] |
|---|---|---|---|---|
| SEQ ID NO: 1 | **C** | T | 60.940.159 | Substitution [T/C] |
| SEQ ID NO: 2 | **T** | C | 60.974.766 | Substitution [C/T] |

TABLE 4-continued

| SNP markers-nucleotides and physical positions | | | | |
|---|---|---|---|---|
| Marker sequence (FIG. 1) | Nucleotide(s) of the SNP in FIG. 1, to be used as marker of the invention | Nucleotide(s) of the SNP in the wildtype (susceptible allele) | physical position of the SNP on the public SL3_00 genome map (wildtype) (in bp) | Type of polymorphism [wildtype/resistance] |
| SEQ ID NO: 3 | **A** | G | 60.975.712 | Substitution [G/A] |
| SEQ ID NO: 4 | **T** | C | 60.977.552 | Substitution [C/T] |
| SEQ ID NO: 5 | **A** | G | 60.982.084 | Substitution [G/A] |
| SEQ ID NO: 6 | **A** | C | 61.034.283 | Substitution [C/A] |
| SEQ ID NO: 7 | **T** | G | 61.080.755 | Substitution [G/T] |
| SEQ ID NO: 8 | **C** | T | 61.080.770 | Substitution [T/C] |
| SEQ ID NO: 9 | **C** | G | 61.080.791 | Substitution [G/C] |
| SEQ ID NO: 10 | **T** | G | 61.081.880 | Substitution [G/T] |
| SEQ ID NO: 11 | **G** | C | 61.081.909 | Substitution [C/G] |
| SEQ ID NO: 12 | **G** | A | 61.098.941 | Substitution [A/G] |
| SEQ ID NO: 13 | **C** | G | 61.124.509 | Substitution [G/C] |
| SEQ ID NO: 14 | **A** | G | 61.124.521 | Substitution [G/A] |
| SEQ ID NO: 15 | **G** | C | 61.124.616 | Substitution [C/G] |
| SEQ ID NO: 16 | **T** | C | 61.136.984 | Substitution [C/T] |
| SEQ ID NO: 17 | **G** | A | 61.153.365 | Substitution [A/G] |
| SEQ ID NO: 18 | **G** | T | 61.153.405 | Substitution [T/G] |
| SEQ ID NO: 19 | **A** | G | 61.154.280 | Substitution [G/A] |
| SEQ ID NO: 20 | **A** | C | 61.167.805 | Substitution [C/A] |
| SEQ ID NO: 21 | **A** | G | 61.167.956 | Substitution [G/A] |
| SEQ ID NO: 22 | **T** | C | 61.175.582 | Substitution [C/T] |
| SEQ ID NO: 23 | **G** | A | 61.187.909 | Substitution [A/G] |
| SEQ ID NO: 24 | **T** | G | 61.192.735 | Substitution [G/T] |
| SEQ ID NO: 25 | **C** | G | 61.202.144 | Substitution [G/C] |
| SEQ ID NO: 26 | **C** | T | 61.251.554 | Substitution [T/C] |
| SEQ ID NO: 27 | **C** | A | 61.252.348 | Substitution [A/C] |
| SEQ ID NO: 28 | **TGCT** | TGCCGCT | 61253155-61253161 | Deletion [GCC/***] |

TABLE 4-continued

SNP markers-nucleotides and physical positions

| Marker sequence (FIG. 1) | Nucleotide(s) of the SNP in FIG. 1, to be used as marker of the invention | Nucleotide(s) of the SNP in the wildtype (susceptible allele) | physical position of the SNP on the public SL3_00 genome map (wildtype) (in bp) | Type of polymorphism [wildtype/resistance] |
|---|---|---|---|---|
| SEQ ID NO: 29 | **C** | T | 61.253.498 | Substitution [T/C] |
| SEQ ID NO: 30 | **TGA** | TGGA | 61254440-61254443 | Deletion [G/*] |
| SEQ ID NO: 31 | **T** | C | 61.257.969 | Substitution [C/T] |
| SEQ ID NO: 32 | **T** | C | 61.258.594 | Substitution [C/T] |
| SEQ ID NO: 33 | **T** | A | 61.258.680 | Substitution [A/T] |
| SEQ ID NO: 34 | **C** | T | 61.268.020 | Substitution [T/C] |
| SEQ ID NO: 35 | **G** | A | 61.319.325 | Substitution [A/G] |
| SEQ ID NO: 36 | **G** | A | 61.320.559 | Substitution [A/G] |
| SEQ ID NO: 37 | **T** | A | 61.330.646 | Substitution [A/T] |
| SEQ ID NO: 38 | **G** | T | 61.331.331 | Substitution [T/G] |
| SEQ ID NO: 39 | **A** | G | 61.339.395 | Substitution [G/A] |
| SEQ ID NO: 40 | **A** | T | 61.341.448 | Substitution [T/A] |
| SEQ ID NO: 41 | **T** | A | 61.380.617 | Substitution [A/T] |
| SEQ ID NO: | **G** | A | 61.388.756 | Substitution [A/G] |
| SEQ ID NO: 43 | **C** | T | 61.250.851 | Substitution [T/C] |
| SEQ ID NO: 44 | **T** | C | 61.251.440 | Substitution [C/T] |

The positions of the SNPs are present on position 101 of the SEQ ID NOS:, as found in FIG. 1, where they are bold and underscored. For SEQ ID NO: 28 the polymorphism to be used as marker is on positions 101-104. For SEQ ID NO: 30 the polymorphism to be used as marker is on positions 101-103. In this way, a deletion of GCC and a deletion of G, respectively, after position 101 when compared to the wild-type sequence can be identified.

SEQ ID NOS: 28 and 30 are technically speaking not SNPs, as they are not Single Nucleotide Polymorphisms, but InDels. SEQ ID NO: 28 has a deletion of nucleotides TGCC starting on position 61.253.155 of the sequence of the wildtype in the public reference genome, which is replaced by a T, leading to an actual deletion of GCC. Positions corresponding to 61.253.155 to 61.253.161 in the wildtype sequence are TGCCGCT, whereas the resistant line has TGCT, i.e. there is a deletion of GCC, as found on positions 101-104 of SEQ ID NO: 28. SEQ ID NO: 30 has a deletion of nucleotides TG starting on position 61.254.440 of the sequence of the wildtype in the public reference genome, which is replaced by a T, leading to an actual deletion of G. Positions corresponding to 61.254.440 to 61.254.443 in the wildtype sequence are TGGA, whereas the resistant line has TGA, i.e. there is a deletion of G, as found on positions 101-103 of SEQ ID NO: 30. For reasons of simplicity, these InDel polymorphisms are also referred to as SNPs in the context of this invention.

Example 2: qPCR Test of ToBRFV Resistant Sources

Sources of phenotypic ToBRFV resistance were infected with ToBRFV and subsequently observed for virus titer. This was done to determine if the resistance was only phenotypic, so there were no symptoms but the virus was still replicating, and the source could therefore be called tolerant, or if the virus titer was really strongly reduced or even absent, and the source was therefore really resistant.

Measuring the virus titer was done through carrying out a qPCR test. In this test, leaf punch samples having around 6 mm in diameter were taken from ToBRFV infected plants. These samples were ground in 500 µl of PBS buffer solution, and 50 µl of the resulting suspension was used in a 96-well KingFisher Flex isolation protocol. Isolation of the leaf material was done using the innuPREP DNA/RNA virus PLUS Kit. The samples were analysed in a 96CFX qPCR thermocycler (Biorad), using a programme of 5 minutes on 50° C. and 20 sec. on 95° C., followed by 40 cycles of 10 sec. on 95° C. and 60 sec. on 60° C. The number of cycles that is necessary to obtain the PCR product is a measurement for the amount of virus that is present in the sample (Cq_ToBRFV). To be able to compare samples having different genetic backgrounds and having different sample sizes, a tomato reference gene, the PHD gene, was included in each PCR run to correct the outcome (Cq_PHD). The final value for each sample, the Cq_corr, is calculated as Cq_ToBRFV−Cq_PHD=Cq_corr. Because the Cq_PHD is usually between 25 and 29, a sample with a very high virus titer that has for example a Cq_ToBRFV of 7 would result in a final Cq_corr of around −20. A sample with a low virus titer would result in a Cq_corr of around −10 to 0.

The primers used in the assay are given in Table 1. The PCR volumes that are used in the assay are given in Table 2.

From five different trials samples of two internal breeding lines (TO1 and TB2), and two sources having phenotypic resistance, i.e. they had no symptoms in bio-assays, were collected. In each trial 5 to 10 plants were included per line. A qPCR analysis was done on each of these samples to determine the virus titer after infection. The first trial, Jordan Winter, was a field trial which was actively inoculated. The other trials were done under controlled conditions, whereby seedlings were inoculated and scored. Some variation was observed between the results of each genotype in different trials, but there was an extremely good correlation between virus titer and genotypes (Table 5). The two tolerant lines scored comparable and had average Cq_corr values of between −14.94 and −19.94. The symptomless source GNL.3919 clearly had to be considered as a tolerant source, since the virus titer was not much lower than in the susceptible breeding lines, with values of between −11.70 and −17.19. The other source, GNL.3951 however scored very convincing and consistent low levels of virus titer in all trials, with average Cq_corr values per trial of between −0.40 and −8.75. It was therefore confirmed that for true resistance, having reduced replication of the virus in the plant, the genetics of GNL.3951 would have to be used.

TABLE 5

Average Cq_corr scores over trials

| | Trial | | | | |
|---|---|---|---|---|---|
| Line | Jordan_Winter Av. Cq_Corr | 19TBRFV34 Av. Cq_Corr | 19TBRFV46 Av. Cq_Corr | 20TBRFV05 Av. Cq_Corr | 20ToBRFV12 Av. Cq_Corr |
| TO1 | −16.07 | −14.94 | −15.43 | nd | −18.86 |
| TB2 | −17.95 | −15.13 | −15.40 | −15.69 | −19.94 |
| GNL.3951 | −1.15 | −5.38 | −8.75 | −0.40 | −4.47 |
| GNL.3919 | −17.19 | −11.70 | −14.01 | −14.78 | nd |

Example 3: qPCR Test of ToBRFV Backcross and F2 Populations and the Deposits

As described in Example 1, initially BC3F2 populations were made between GNL.3951 and susceptible *S. lycopersicum* line TB2. Virus titer was determined in samples from bio-assays for ToBRFV on these populations, and it was found the titer was not comparably to the GNL.3951 source. Therefore a new cross was made between the BC3F2 and GNL.3951, and this F1 was selfed to obtain F2 populations.

Again, three of the F2 populations were infected with ToBRFV to observe virus symptoms. In these three F2 populations, resulting from three F1 plants, phenotypic virus resistance was found to be present. However, when a qPCR assay was done to determine virus titer, one of the F2 populations showed clear segregation in virus titer, while the other two had virus titer levels comparable to the resistant source (FIG. 2). It was concluded that the true resistance, i.e. the reduction of virus replication, could not necessarily be determined through a bio-assay, but had to be confirmed with a test determining virus titer. It was also confirmed that it was possible to obtain true resistance, i.e. reduction of virus titer, in *S. lycopersicum* plants.

Figure 3:
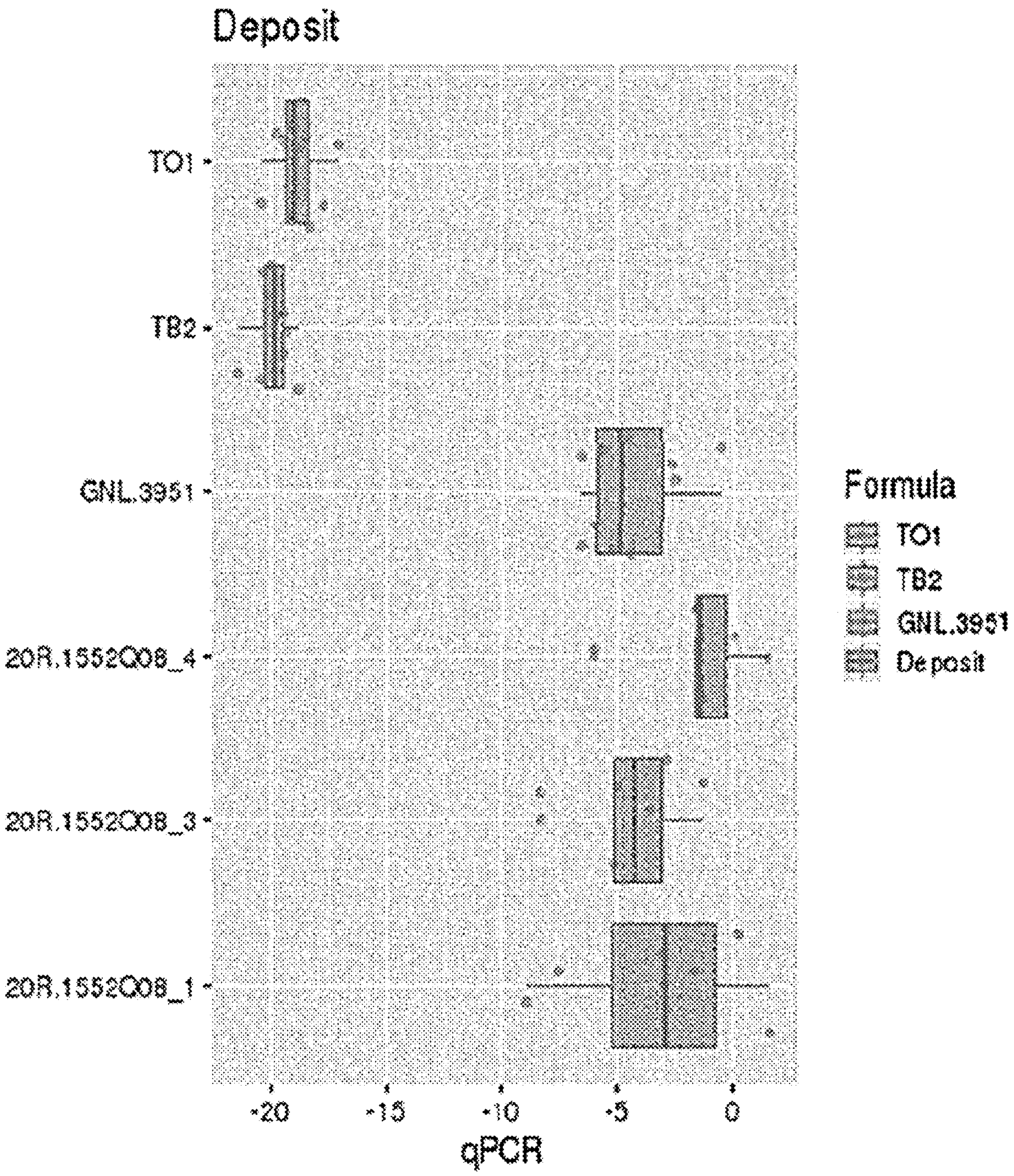

From one of the F2 populations that did not segregate for virus titer in the qPCR, F3 populations were obtained through selfing. Using the parallel developed markers from the QTL analysis, as described in Example 1, plants were confirmed to have the QTL on chromosome 8 linked to the markers of Table 4. Again, plants were infected with ToBRFV and a qPCR analysis for virus titer was done. It was confirmed that also the F3 populations had a reduction of virus replication, so the resistance was maintained in these plants (FIG. 3). The markers developed for the QTL on chromosome 8 were found to co-segregate with the reduction of virus titer, and can therefore be used to identify the reduction in virus titer. One of these F3 populations, 20R.1552Q08_4, was subsequently deposited for this invention, as NCIMB 43637.

Example 4: Identification of Tom2a as the Causal Gene for ToBRFV Resistance

To determine the actual gene within the QTL region on chromosome 8 that conferred the ToBRFV resistance, first a further fine-mapplng step was carried out with recombinants, i.e. lines that had recombinations in the QTL region, derived from the originally used lines. After phenotyping of the recombinants, the involved QTL region was shortened to a region between the markers presented as SEQ ID NO: 22 and SEQ ID NO: 34. Within this region, seven putative genes were present (FIG. 4).

Initially the markers having SEQ ID No, 26, SEQ ID NO: 29, and SEQ ID NO: 30 were identified as the most preferred, and these markers were present within one of those genes, identified as Solyc08g077220.3 in the S13_00 genome, which is named Tom2a. The goal was to confirm this gene as the resistance conferring gene in the material. The resistance is conferred by the allele of the gene as disclosed herein.

In the newly developed set of lines, again selfings were made to obtain further recombinants. These recombinants were analyzed with 13 markers that were present in the region (SL001-SL013 of FIG. 4), and it was found that the population included plants having recombinations on both sides of the Tom2a gene. A recombination between SL004 and SL005 separated the genes left of Solyc08g077220.3 from the region. A recombination between SL009 and SL010 separated Solyc08g077220.3 from Solyc08g077230.3. Phenotyping of these recombinants was done to determine if indeed the resistant phenotype could be linked to the presence of the Tom2a gene.

FIG. 4 shows the marker profiles and phenotyping scores of the recombinant lines. The indicated genes within the region are identified based on the annotation of the public ITAG3.2 reference, which can for example be found on the solgenomics web site. The phenotypes of all 12 recombinants, except 07, deviated from what would be expected if the cluster of genes left from SL005 would contain the causal gene. These genes could therefore be ruled out. The phenotype of recombinant 07 was in line with the expectation of Solyc08g077220.3, i.e. Tom2a, being the causal gene for the ToBRFV resistance. Through these observations, it was indeed confirmed that the allele of the Tom2a gene in the resistant material was causing the ToBRFV resistance in the tomato lines.

Example 5: Virus Titer of Material with the QTL on Chr 8 and a QTL on Chr 11

Isogenic lines were made through development of a BC2F3 population. A line having the QTL of the invention which comprises the resistance conferring Tom2a allele, a line having a QTL on chromosome 11 as described in WO2019110821, a line having the combination of the QTLs on chromosomes 8 and 11, and a line having the susceptible version of the QTLs on chromosomes 8 and 11, were inoculated and analysed, together with the susceptible parent that was used in the cross for the development of the isogenic BC2F3 lines. The QTL on chromosome 11 comprised a resistance conferring CCA gene and/or a resistance conferring Albino3-like gene. After inoculation, qPCR analysis for virus titer was performed, as described in Example 2.

Figure 7:
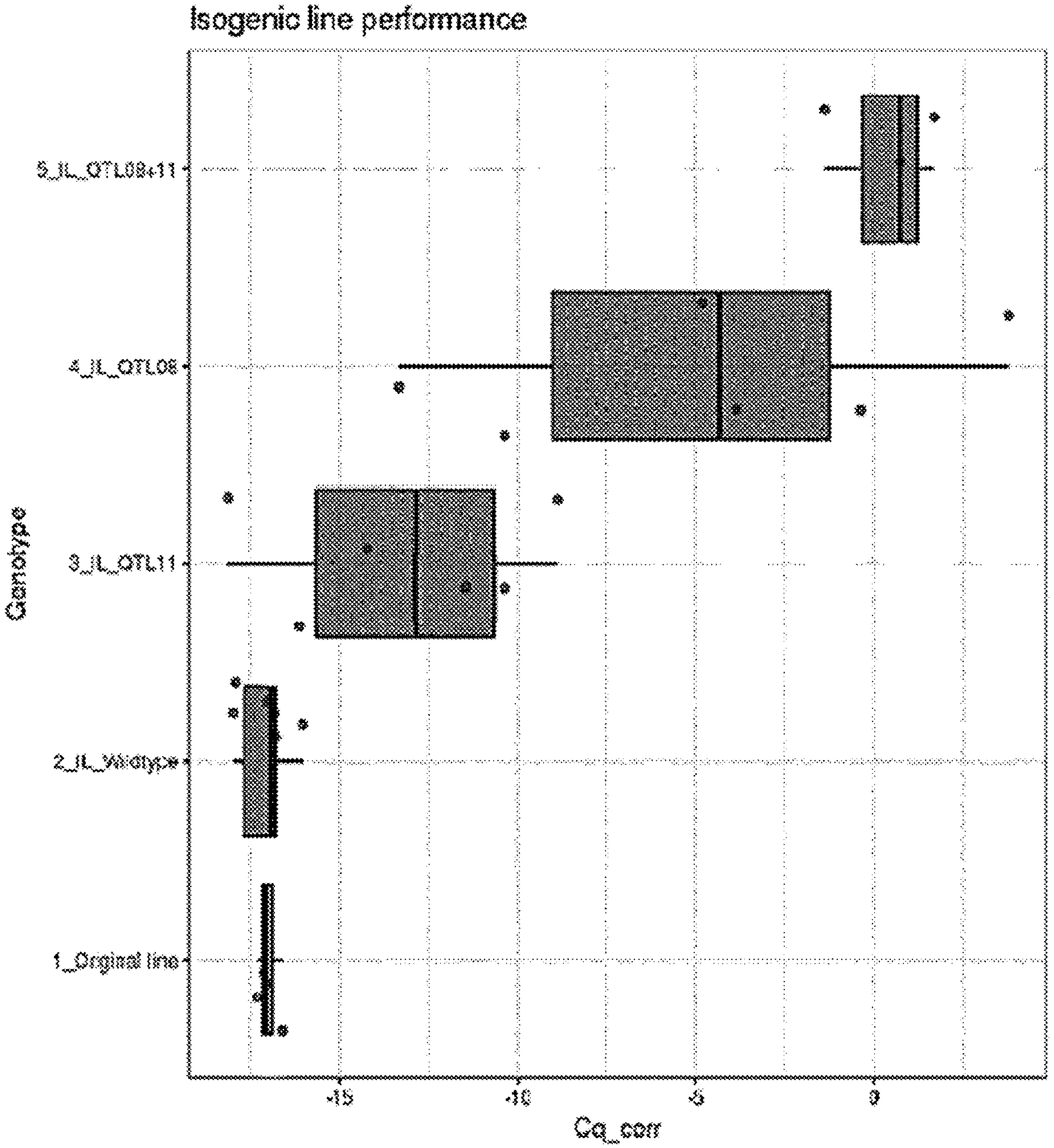

Results are presented in FIG. 7. It was found that the reduction of virus titer in the line having the resistance conferring Tom2a allele (4_IL_QTL08) was even further reduced when it was combined with the QTL on chromosome 11 (5_IL_QTL08+11). This was a very surprising effect, since a line with only the QTL on chromosome 11 (3_IL_QTL11) had limited reduction of virus titer. The isogenic line lacking both resistance QTLs (2 IL Wildtype) had a similar virus titer as the susceptible parent (1 Original line). Therefore, it was concluded that a stronger and more durable resistance in tomato can be obtained by combining the QTLs of chromosomes 8 and 11. A stronger and more durable ToBRFV resistance can in particular be obtained through a combination of a resistance conferring Tom2a allele combined with a resistance conferring CCA gene or combined with a resistance conferring Albino3-like gene.

The invention is further described by the following numbered paragraphs:

1. A *Solanum lycopersicum* plant comprising a QTL on chromosome 8, wherein the QTL on chromosome 8 is located between SEQ ID NO: 1 and SEQ ID NO: 42, which QTL confers ToBRFV resistance when homozygously present.

2. A *Solanum lycopersicum* plant of paragraph 1, wherein the QTL comprises a resistance conferring Tom2a allele, which resistance conferring Tom2a allele comprises SEQ ID NO: 45, or comprises a homologous Tom2a sequence having at least 70% sequence identity to SEQ ID NO: 45.

3. A *Solanum lycopersicum* plant of paragraph 1 or 2, wherein the presence of the QTL on chromosome 8 is genetically linked to at least one of the markers selected from the group consisting of the SNP presented in SEQ ID NOS: 1 to 44, preferably by a marker selected from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, SEQ ID NO: 42, SEQ ID NO: 43, and SEQ ID NO: 44, most preferably by a marker selected from the group consisting of SEQ ID NO: 26, SEQ ID NO: 27, SEQ ID NO: 28, SEQ ID NO: 29, SEQ ID NO: 30, SEQ ID NO: 43, and SEQ ID NO: 44.

4. A *Solanum lycopersicum* plant of paragraph 1, 2 or 3, wherein the QTL is as present in the genome of a *Solanum lycopersicum* plant representative seed of which was deposited with the NCIMB under deposit number NCIMB 43637.

5. A *Solanum lycopersicum* plant of paragraph 1, 2 or 3, wherein the QTL is introgressed from NCIMB 43637 or from a progeny plant thereof.

6. A *Solanum lycopersicum* plant of paragraph 1, 2 or 3, wherein the QTL is introgressed from a plant of the species *Solanum pimpinellifolium*, or from a plant of another *Solanum* species that is sexually compatible with *S. lycopersicum*.

7. A *Solanum lycopersicum* plant of any of the paragraphs 1-6, wherein the QTL is present homozygously.

8. A cell of a *Solanum lycopersicum* plant of any one of the paragraphs 1-7, which cell comprises the QTL on chromosome 8 as defined in any one of the paragraphs 1-3 in its genome.

9. A *Solanum lycopersicum* seed comprising the QTL on chromosome 8 as defined in any of the paragraphs 1-4, wherein a plant grown from the seed is a plant of any one of the plants of paragraphs 1-7.

10. Propagation material suitable for producing a *Solanum lycopersicum* plant of any one of the paragraphs 1-7, wherein the propagation material is suitable for sexual reproduction, and is in particular selected from the group consisting of a microspore, pollen, an ovary, an ovule, an embryo sac, and an egg cell; or is suitable for vegetative reproduction, and is in particular selected from the group consisting of a cutting, a root, a stem, a cell, and a protoplast; or is suitable for tissue culture of regenerable cells, and is in particular selected from the group consisting of a leaf, pollen, an embryo, a cotyledon, a hypocotyl, a meristematic cell, a root, a root tip, an anther, a flower, a seed, and a stem; wherein the plant produced from the propagation material comprises the QTL on chromosome 8 that leads to ToBRFV resistance as defined in any one of the paragraphs 1-4.

11. Marker for the identification of ToBRFV resistance in a *Solanum lycopersicum* plant, or in a *Solanum pimpinellifolium* plant, or in a plant of another *Solanum* species that is sexually compatible with *S. lycopersicum*, which marker is selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 28, SEQ ID NO: 43, and SEQ ID NO: 44.

12. Marker for the identification of a QTL on chromosome 8 that leads to ToBRFV resistance in a *Solanum lycopersicum* plant, or in a *Solanum pimpinellifolium* plant, or in a plant of another *Solanum* species that is sexually compatible with *S. lycopersicum*, which marker is selected from the group consisting of the SNP presented in SEQ ID NOS: 1 to 44, preferably from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44, most preferably by a marker selected from the group consisting of the SNP presented in SEQ ID NO: 26, SEQ ID NO: 29, and SEQ ID NO: 30.

Use of a marker of paragraph 11 or 12 for identification of ToBRFV resistance in a *Solanum lycopersicum* plant, or in a *Solanum pimpinellifolium* plant, or in a plant of another *Solanum* species that is sexually compatible with *S. lycopersicum*.

14. Method for producing a ToBRFV resistant *Solanum lycopersicum* plant comprising introgressing a QTL on chromosome 8 as defined in any of the paragraphs 1~4 into a *S. lycopersicum* plant.

15. Method for selecting a ToBRFV resistant *Solanum lycopersicum* plant, or a *Solanum pimpinellifolium* plant, or a plant of another *Solanum* species that is sexually compatible with *S. lycopersicum*, comprising identifying the presence of a QTL on chromosome 8 as defined in any of the paragraphs 1-4, and selecting a plant that comprises said QTL as a ToBRFV resistant plant.

16. Method of paragraph 15, wherein identifying the presence of the QTL on chromosome 8 is done by using a marker selected from the group consisting of the SNP presented in SEQ ID NOS: 1 to 44, preferably from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, SEQ ID NO: 42, SEQ ID NO: 43, and SEQ ID NO: 44, most preferably by a marker selected from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44.

17. A method for the production of a *Solanum lycopersicum* plant which is resistant to ToBRFV, said method comprising:

a) crossing a plant of any one of the paragraphs 1-6 comprising the QTL on chromosome 8 with another plant;
b) optionally performing one or more rounds of selfing and/or crossing of the plant resulting from the cross in step a) to obtain a further generation population;
c) selecting from the plant resulting from the cross in step a), or from the further generation population of step b), a plant that comprises the QTL on chromosome 8, as defined in any one of the paragraphs 1-4, which plant is resistant against ToBRFV when the QTL is homozygously present.

18. Method of paragraph 17, wherein selection of a plant comprising the QTL on chromosome 8 is done by using a molecular marker genetically linked to the QTL, which marker is selected from the group consisting of the SNP presented in SEQ ID NOS: 1 to 44, preferably from the group consisting of the SNP presented in SEQ ID NO: 3, SEQ ID NO: 4, SEQ ID NO: 14, SEQ ID NO: 16, SEQ ID NO: 17, SEQ ID NO: 18, SEQ ID NO: 19, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID No, 34, SEQ ID NO: 42, SEQ ID NO: 43, and SEQ ID NO: 44, most preferably by a marker selected from the group consisting of the SNP presented in SEQ ID NO: 26, SEQ ID NO: 27, SEQ ID NO: 28, SEQ ID NO: 29, SEQ ID NO: 30, SEQ ID NO: 43, and SEQ ID NO: 44.

19. Method of paragraph 17, wherein the plant which is resistant to ToBRFV is phenotypically selected, in particular by using a bio-assay for ToBRFV resistance, or is selected using a qPCR test.

20. Method of any one of the paragraphs 17-19, wherein the plant of any one of the paragraphs 1-7 is a plant grown from seed deposited under NCIMB accession number NCIMB 43637, or a progeny plant thereof.

21. Method for the production of a *Solanum lycopersicum* hybrid seed comprising crossing a first parent plant with a second parent plant and harvesting the resultant hybrid seed, wherein the first parent plant and the second parent plant are a plant of the invention that is resistant to ToBRFV comprising the QTL on chromosome 8 as defined in any of the paragraphs 1-4, wherein the presence of the QTL leads to resistance to ToBRFV in the hybrid plant that is grown from the seed.

22. The hybrid seed produced by the method of paragraph 21.

23. Resistance conferring Tom2a allele comprising SEQ ID NO: 45, or comprising a homologous Tom2a sequence having at least 70% sequence identity to SEQ ID NO: 45.

24. Resistance conferring Tom2a allele of paragraph 23 which encodes a protein comprising SEQ ID NO: 46, or encodes a homologous protein having at least 70% sequence identity to SEQ ID NO: 46.

25. Resistance conferring Tom2a allele of paragraph 23 or 24, wherein the homologous sequence encodes a protein comprising at least one of a deletion of Ala on position 105 of SEQ ID NO: 48, a conversion from Arg to Gly on position 187 of SEQ ID NO: 48, a conversion from Gly to Ser on position 225 of SEQ ID NO: 48, or a conversion from Thr to Ala on position 282 of SEQ ID NO: 48.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a QTL on chromosome 8 that leads to Tomato brown rugose fruit virus (ToBRFV) resistance in a plant, comprising identifying a marker in the plant, wherein:

the plant is a *Solanum lycopersicum* (*S. lycopersicum*) plant, or a *Solanum pimpinellifolium* plant, or a plant of another *Solanum* species that is sexually compatible with *S. lycopersicum*; and the marker is located between SEQ ID NO: 1 and SEQ ID NO: 42, and comprises SEQ ID NO: 28 and/or a GGC deletion at the position corresponding to positions 312-314 of SEQ ID NO: 47.

2. A method for selecting a Tomato brown rugose fruit virus (ToBRFV) resistant plant, comprising identifying the homozygous presence of a QTL on chromosome 8 of a plant, and selecting the plant that homozygously comprises said QTL as a ToBRFV resistant plant, wherein:

the plant is a *Solanum lycopersicum* (*S. lycopersicum*) plant, or a *Solanum pimpinellifolium* plant, or a plant of another *Solanum* species that is sexually compatible with *S. lycopersicum*; and identifying comprises identification within the QTL of the presence of SEQ ID NO: 28 and/or identification within the QTL of a GGC deletion at the position corresponding to positions 312-314 of SEQ ID NO: 47.

3. The method of claim 2, wherein identifying further comprises identification within the QTL of the presence of a guanine (G) at the position corresponding to 559 of SEQ ID NO: 47, an adenine (A) at the position corresponding to 673 of SEQ ID NO: 47, and/or a guanine (G) at the position corresponding to 844 of SEQ ID NO: 47.

4. A method of selecting a *Solanum lycopersicum* plant or plant part that exhibits increased resistance to Tomato brown rugose fruit virus (ToBRFV), comprising:

a) identifying in a *Solanum lycopersicum* plant or plant part by genetic analysis the homozygous presence of a QTL on chromosome 8 located between SEQ ID NO: 1 and SEQ ID NO: 42, wherein identifying comprises identification within the QTL of the presence of SEQ ID NO: 28, and/or identification within the QTL of a GGC deletion at the position corresponding to positions 312-314 of SEQ ID NO: 47; and b) selecting a plant or plant part from a) that comprises said QTL homozygously, optionally testing the selected plant or plant part for increased resistance to ToBRFV as compared to a *Solanum lycopersicum* plant or plant part that does not comprise said QTL homozygously, wherein the selected plant or plant part does exhibit increased resistance to ToBRFV as compared to a *Solanum lycopersicum* plant or plant part that does not comprise said QTL homozygously.

5. The method of claim 4, wherein identifying further comprises identification within the QTL of the presence of a guanine (G) at the position corresponding to 559 of SEQ ID NO: 47, an adenine (A) at the position corresponding to 673 of SEQ ID NO: 47, and/or a guanine (G) at the position corresponding to 844 of SEQ ID NO: 47.

* * * * *

SEQUENCE LISTING

```
Sequence total quantity: 54
SEQ ID NO: 1           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 1
tgtaaactta acattaatgt ttacttagat attttaacta gatttagaca cctaatgtca  60
gatttcagta tgttattttg acactttttt acaccatcaa caaaaatata taatgtaaat  120
atgttatact tattaataac gtgtaaaata tcaaactaaa tgataacact tatcattttg  180
tgtccaaaat aatactaaaa t                                            201

SEQ ID NO: 2           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 2
ttttayatat ttcacttaag gcaccaatgg atcaacacct tcatatgtat atcacccaaa  60
tttctcaatt gacggcggtg aatatttgca ctttagacct ttgcaagtca tttccttatt  120
ctgtygacac tacattaaaa atgattttta gtgtcaatta attaacggta atactttcga  180
aatatatatt tttagcagca a                                            201

SEQ ID NO: 3           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 3
ttcatcgtat taatatgcaa aaaaaktaaa tttataatac tttttctata atttttgaaa  60
atctaattat atttttaaa tatcaaatta atataatcta atttaatttt gaaaaattaa  120
tcaaattgac tttyaataag tgcaacatga tacttaaaaa gtggatggaa gaagtaatca  180
actgcaacgg tatgtttgga a                                            201

SEQ ID NO: 4           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 4
gattacttgt ctaattaatt attgatataa ttttaagtag tttacgaact agagagtata  60
tttaaaataa ataattattt actaaaagag attcactcaa tataaactat aaataacaag  120
attacaacat gaagacgtgc aaagatgtta ggccttatga taaagaataa ggaataaaat  180
cttttttagc atttcgttta g                                            201

SEQ ID NO: 5           moltype = DNA  length = 201
FEATURE                Location/Qualifiers
```

```
misc_feature           1..201
                       note = SNP marker
source                 1..201
                       mol_type = genomic DNA
                       organism = Solanum lycopersicum
SEQUENCE: 5
ttaactaaac amwtaaaatg tatttaaaac tagctattcc ttttaatcaa tgtataatat  60
atgtgacagt attaaactgg acataagata taagaaatat aaaaaractt agcaatgttt  120
taaaatatct ttaaaagaat atataaatat ttgtgattat tttgagcaaa taaatggtaa  180
acatagatgg aatattgata a                                            201

SEQ ID NO: 6           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 6
aatcaaaatt ttataaaatt gaaccgaaga atcaaaagtc cactcctagt cttagggtct  60
aaagartttt ttgtagggga gaatttgtgg gagtgaatct atttgtactt cgagcgaatt  120
gtgtgagctt aytccttttt atcatttgga cttttttaa taaagtggat tgttcatctc  180
ctctyatcaa gtgaccgtat c                                            201

SEQ ID NO: 7           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 7
artcatttg ttttatgaga tatagaaata aaatttaatt atattttatt cttctcarat  60
tctacgtgta aaattaccat aaatataact attattaaga ttgtttaaga gaagaygtaa  120
tgactttgca caaagtsgtt gttaatataa ggatccactt gtcctcgaac gtaattcatt  180
gtcaaaattt tgtctctatt t                                            201

SEQ ID NO: 8           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 8
tgagatatag aaataaaatt taattatatt ttattcttct carattctac gtgtaaaatt  60
accataaata taactattat taagaktgtt taagagaaga cgtaatgact ttgcacaaag  120
tsgttgttaa tataaggatc cacttgtcct cgaacgtaat tcattgtcaa aattttgtct  180
ctattttcaa acgcgcttag a                                            201

SEQ ID NO: 9           moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 9
aattatattt tattcttctc arattctacg tgtaaaatta ccataaatat aactattatt  60
aagaktgttt aagagaagay gtaatgactt tgcacaaagt cgttgttaat ataaggatcc  120
acttgtcctc gaacgtaatt cattgtcaaa attttgtctc tattttcaaa cgcgcttaga  180
tgcragttta atttaccaac t                                            201

SEQ ID NO: 10          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 10
tcatttttta aaataatatt tatatatttr taaattatgt aaaaagataa tataagtcaa  60
aataattggc aattcaaaat ggttgaaaga tatataaaaa tttcacgata aaaataataa  120
ttgaaatcts aacatccaaa aaaaatcaca taattaagac ggaggagaaa atatcatctt  180
tttaaatttc aattatataa c                                            201

SEQ ID NO: 11          moltype = DNA  length = 201
FEATURE                Location/Qualifiers
misc_feature           1..201
```

```
                        note = SNP marker
source                  1..201
                        mol_type = genomic DNA
                        organism = Solanum lycopersicum
SEQUENCE: 11
rtaaattatg taaaaagata atataagtca aaataattgg caattcaaaa tggttgaaag  60
atatataaaa akttcacgat aaaaataata attgaaatct gaacatccaa aaaaaatcac  120
ataattaaga cggaggagaa aatatcatct ttttaaattt caattatata actatactga  180
atatattatt attaccacgg t                                            201

SEQ ID NO: 12           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 12
tttgttttga ttgtatcgta tagtattata atttataaat ttastaaaat atcgttaatc  60
attctaggga atgaggtttg actagattta aataattaag gtaaagggta aaatagtatt  120
ttgaaatatt acgtaaagat ataattggaa aaagaaatta agtaacaatg cgaaaacacc  180
aaatcggttg ttccataaaa t                                            201

SEQ ID NO: 13           moltype = DNA  length = 201
FEATURE                 Location/Qualifiers
misc_feature            1..201
                        note = SNP Marker
source                  1..201
                        mol_type = genomic DNA
                        organism = Solanum lycopersicum
SEQUENCE: 13
aaaaattctt tgaatgaagt agaattctaw atgataaaaa tttaaaataa ttaaatttta  60
atgaaataca ctgacaaata gggctgtgta tcgatcgatt cggtttaatt ttraagttta  120
tcggattggc ttattggtta tyggtttata atgatgctaa atcattatag aaccattaar  180
atattgactt atcggttatt g                                            201

SEQ ID NO: 14           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 14
aatgaagtag aattctawat gataaaaatt taaaataatt aaattttaat gaaatacact  60
gacaaatagg gctgtgtatc gatcgattsg gtttaatttt aaagtttatc ggattggctt  120
attggttaty ggtttataat gatgctaaat cattatagaa ccattaarat attgacttat  180
cggttattgg tttatsggtt t                                            201

SEQ ID NO: 15           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 15
attttraagt ttatcggatt ggcttattgg ttatyggttt ataatgatgc taaatcatta  60
tagaaccatt aaratattga cttatcggtt attggtttat gggtttttga tcgttatcgg  120
tttaaccgtt aagatttgam tcaaaaraaa aaatattgaa aatcacttag aaacaaggtg  180
acaaatcaaa taaaccatgc a                                            201

SEQ ID NO: 16           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 16
ttttaattta atattggtat atataaaagt tggacctcct aaaataattt agtaagacac  60
aatagagttg gcaatagcta gggcatccct acactttgtc tgggtttgat ttcccgcggg  120
atgtttcatt tttctttaat tatttttgac aattttatta ttaaaaaaac atgcttastc  180
ttaacataaa catttagtag t                                            201

SEQ ID NO: 17           moltype = DNA  length = 201
FEATURE                 Location/Qualifiers
misc_feature            1..201
                        note = SNP marker
```

-continued

```
source                  1..201
                        mol_type = genomic DNA
                        organism = Solanum lycopersicum
SEQUENCE: 17
cacaaattat tagattcatt tctgaactat taacagcctt gaaaacacct ctctactaay  60
atagcaagcg atctcaaact cttatatgaa yatgagactt gtaataaaaa gctgagagaa  120
gtgttgaaaa cactcctaaa ktagtgatgt actgcattca tgatgcaaga tcggrgatgt  180
attttatcct tcagggttgy c                                            201

SEQ ID NO: 18           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 18
gaaaacacct ctctactaay atagcaagcg atctcaaact cttatatgaa yatgagactt  60
rtaataaaaa gctgagagaa gtgttgaaaa cactcctaaa gtagtgatgt actgcattca  120
tgatgcaaga tcggrgatgt attttatcct tcagggttgy ccagtgttac ctcgcctatt  180
tagtttgcgc tctattgagt a                                            201

SEQ ID NO: 19           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 19
aataaartag tacacattgt ttggtcaaac aatttggtga ttttttgaaa atatatcttc  60
aaaaattaat caaacttcaa aatctggtcr tgaaatatca atttcattca tagaatttta  120
atttatttgc agagaaaatg tagggataag agtytgaaaa atatctcaat tttgatcgaa  180
tttgttcttg cgatacttaa c                                            201

SEQ ID NO: 20           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 20
gccagatgac agactttgtg gatgcttact ctcagttgtg tcctactgca agggcgacga  60
tgcagataag gtccttgctt gtctacaaca agctaaccca agattggtaa cctttgtcaa  120
gatgctagaa gatgagagca ctagctatga cattgtgaaa gaagagttca ggtccatact  180
gactaataca tcagatgatg c                                            201

SEQ ID NO: 21           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 21
attgtgaaag aagagttcag gtccatactg actaatacat cagatgatgc tagaaggccc  60
ttctgtaatt gtctaattga tatatgcaga aagagaaatc acgcagagag ggctcacgag  120
cttctatact tgggaactgt atatggacta tacccaggtt tacatactaa gacaccagaa  180
gaatggcgat traacgtccg a                                            201

SEQ ID NO: 22           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 22
taaatataaa taaatcgttc aagtttgtta cgatccaaaa aygaggcttg artgrcactc  60
acacttatcc tactatgtga gcgaaccaac ccatctaaay tccaacattt caaaacataa  120
tagacagaat ataatgygga agacttaaaa ctcattaacg aagtcaataa ttaacttcta  180
aaactcaaaa cttatcatta t                                            201

SEQ ID NO: 23           moltype = DNA  length = 201
FEATURE                 Location/Qualifiers
misc_feature            1..201
                        note = SNP marker
source                  1..201
```

```
                        mol_type = genomic DNA
                        organism = Solanum lycopersicum
SEQUENCE: 23
ttaatargac tccttacaag cgttgtttct atctactatt atctaaaaat aatcaagtta  60
ttaatgaccg gacgaaacaa agaaataacc cctcatgtgc gaaattatag aagatcccct  120
ttaagatcaa acaattccat mraattgagt atgattgtat gtgtgatagc atctactata  180
ccaggaatat caatgaaccc g                                            201

SEQ ID NO: 24           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 24
aagaggccgt ggtagaggtc gtgggaggac gtcctctaga ggaaggggac gagcacctag  60
cccatctgat actagggcgg tgactcctcc accgactgaa taagtagtaa tagaagggga  120
ggatggggaa aatgaacaag tacagaatga ggaattacca ccccaaccta ccccagaaat  180
gatcaatcag gttcttgctt a                                            201

SEQ ID NO: 25           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 25
taacttatat ttgtaaataa atctcatgtt taactcaaac tcaaaaagca acsacactat  60
cataaaaata aaaagtcact catccttaaa gggacaattc cggactcatt aaattcctcg  120
aactcaatct gaatctagac atctaatgca taaacaattt aatataaaaa gtcctacacc  180
aaaaaataaa aaatggaata a                                            201

SEQ ID NO: 26           moltype = DNA  length = 201
FEATURE                 Location/Qualifiers
misc_feature            1..201
                        note = SNP marker
misc_feature            198..201
                        note = /note="n = a or t or c or g"
source                  1..201
                        mol_type = genomic DNA
                        organism = Solanum lycopersicum
SEQUENCE: 26
gctggtggcc tattgttgat cagtggctgt cggatttgtt gtctgggacc acctatgtac  60
tcatcatcac tatcatartc tgctggtctg tttgctgccc ctactacgag ggccaataag  120
aatataagag cctgcaactc atgtaaacrg acgaaactga gagactygga gaaaattaag  180
acaaacaatt ttcaggtnnn n                                            201

SEQ ID NO: 27           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 27
tcgtttcaaa gttgcccgtt ttatcccttg gaatttcctg acaaagactt tcatcacttt  60
tctgacaaca aagtatagtw tgaaagtgaa gtcgtgagtg cgaaaacact tacatctttc  120
cagcttttat caaagaatat aaaaccagca gcacctagct ctaccaagat caacaagaaa  180
atcaacatgg agtactgttc c                                            201

SEQ ID NO: 28           moltype = DNA  length = 201
FEATURE                 Location/Qualifiers
misc_feature            1..201
                        note = Indel marker
source                  1..201
                        mol_type = genomic DNA
                        organism = Solanum lycopersicum
SEQUENCE: 28
tatgtgggct gtatattttt taaattttcc cataaataat aaatcaagaa gactgaacaa  60
atgataagga tacacaactc aggcagcaac cattccttgt tgctccaata caaccacagc  120
aagatacaac tacaagaact gctccaatac caataaacaa atatatgaac ctgcgacata  180
acaaatgggt caatgcttca t                                            201

SEQ ID NO: 29           moltype = DNA  length = 201
FEATURE                 Location/Qualifiers
misc_feature            1..201
                        note = SNP marker
```

```
source                  1..201
                        mol_type = genomic DNA
                        organism = Solanum lycopersicum
SEQUENCE: 29
trcaaatcat gtagtcaagt tctgagaatt cacacccact gaccactcaa aacttggaaa  60
atattatgag actctgttaa taattcaata wtggacaagc ccaaacaggt gaagamcata  120
tatagttcct ttttcttatt tatacttcca tgtttcttta gctctacacc trggaaacat  180
atgattcaac cttcgcatat a                                            201

SEQ ID NO: 30           moltype = DNA  length = 200
FEATURE                 Location/Qualifiers
misc_feature            1..200
                        note = Indel marker
source                  1..200
                        mol_type = genomic DNA
                        organism = Solanum lycopersicum
SEQUENCE: 30
agaggatgta ayagaatgaa ctctcagtat ttttaactgg ttcaagacta ctttggrttt  60
tcagagattt taactcaata agttccctag ggaaaagaga tgaatgtgat tctttatcta  120
gtgtaatagt tcttggagat tttattgatt atccgttgac tgatgataag ttctccaaat  180
caaggagtca aagtgaagat                                              200

SEQ ID NO: 31           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 31
tgtatatctr gmgagcgaga ttaagagagg gatgaaagag gcaagtgtga ttgggagaga  60
gaggagagag actaattgta tttgtatatc tttcatataa ttgtatgtat aaatgtacaa  120
tttgtatttg tatatggatt agcaacctaa ttacaactaa aattaagttg tgagtcgtaa  180
ttaattcaaa ctatagctac a                                            201

SEQ ID NO: 32           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 32
aatttgtata aaatgagaaa gagagaaaga taaaagagac ttgacaagga atatacaatt  60
raatcgaatt gtataaaatg agaaagagag aaagtaaata tawtttgaaa attgtataag  120
acgagaaaga gagaagggca aaagaaastg ggyagaggag tatttttatt gtataattat  180
aattgtwtag gacgaaaata t                                            201

SEQ ID NO: 33           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 33
agagaaagta aatayawttt gaaaattgta taagacgaga aagagagaag ggcaaaagaa  60
astgggyaga ggagtatttt tattgtataa ttataattgt ttaggacgaa aatatatgta  120
cgtgcatgtg tatatacaat tttctcacgc tttatayaaa cagaaaygca atttatacat  180
ttcgcttctg tttgtacaag t                                            201

SEQ ID NO: 34           moltype = DNA  length = 201
FEATURE                 Location/Qualifiers
misc_feature            1..201
                        note = SNP marker
source                  1..201
                        mol_type = genomic DNA
                        organism = Solanum lycopersicum
SEQUENCE: 34
aatatacatc aattttttat attayttttc atatagtgtt tttaaatatt tttattttca  60
atratatttc tcgtaacata gccacatatc taataaaata cttttatttt tgtaattttt  120
aatttttaaa tacgagggtt tgtgactgac caacrtacsg actactctac cacgtatata  180
caacatagtt ggaaagaatt t                                            201

SEQ ID NO: 35           moltype = DNA  length = 201
FEATURE                 Location/Qualifiers
misc_feature            1..201
                        note = SNP marker
source                  1..201
```

```
                       mol_type = genomic DNA
                       organism = Solanum lycopersicum
SEQUENCE: 35
caaagctaaa tcctccccac tactccatcc actctccacc gccttttyg cctccacatt  60
ttcgaaatca gcctcatttc caccctcagc tctcttatca gcygttttcc tgtccttcaa  120
aaacctctga taggaatccc catcactcat tttcttctca cccaattctt tagatttctt  180
aatcacactt tccactttgt a                                           201

SEQ ID NO: 36          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 36
tcttgttggt tgttatattt tcaacattgt tttctttttc tttgtacttg aatttgttgt  60
tattaatcga acatctttga aaaacaatct atctacctcg gcaaggtaat gatatgattc  120
gtctatattc taccatcttc gaatcgtgct tatggaattt cacgctaagg aaaccttttc  180
aatacatgag aagcgcagtg t                                           201

SEQ ID NO: 37          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 37
tttctggcag ggctggtggt tcttttgatg ataggaggtt tctagacgat agattttcaa  60
gggatggtgt ttatccccgg ggtgcctatc accgtgatat tctggatgga gagcactacc  120
ctcatccacc agcagcagtt ggacactggc ctcagacaag gaggagaagt tatgaagaag  180
tgtaccctgt ggagagggat t                                           201

SEQ ID NO: 38          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 38
ccgatacgat agaagtgaga gacgaagaga tcgtgatgat aaaagatacc atgacaatta  60
ttctgtggta tgtttcctgt ttcttatgtt gcacttccca gttgctttta tgtttggagg  120
ggctcatggc ttctgttatt ttaatgcagg ctccttcagc gactgttgtt gtcaaaggcc  180
tttcacaaaa aactactgaa g                                           201

SEQ ID NO: 39          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 39
tattattgct tgggcttcaa gatcgggact caacattcag aagaggtgtt tttgatccaa  60
ctcctttccc ccctggtgty ggaggtggac gtagtgcaga agcgaatagt cagagctttg  120
aggttatcac ggctgacagg gctatagacg agagtaaygt gggcaatcgt atgcttcgca  180
acatgggatg gcaggagggc t                                           201

SEQ ID NO: 40          moltype = DNA  length = 201
FEATURE                Location/Qualifiers
misc_feature           1..201
                       note = SNP marker
source                 1..201
                       mol_type = genomic DNA
                       organism = Solanum lycopersicum
SEQUENCE: 40
ttcaacaccc tttagctgca ggtagagtta tgatgaagct ctgttcttca caatccactt  60
ttcctcatgc tgtaaagatt tttgagaatc ttgaataccc agatgctttt atttgtaata  120
cagttatgaa atgttatgtg aatttcgatg acccggaaaa gggtttggtg ttttattctg  180
atcagatggt taaaaatggg a                                           201

SEQ ID NO: 41          moltype = DNA  length = 201
FEATURE                Location/Qualifiers
misc_feature           1..201
                       note = SNP marker
source                 1..201
                       mol_type = genomic DNA
```

```
                         organism = Solanum lycopersicum
SEQUENCE: 41
tacaaataat gtcgtgtatg gaataaactt gcttacaatt caatggttct atgaaacaga  60
aattaggtaa aatctgttct rtagtttgtt aagtatattg taaaaataaa atttctttat  120
atgtggttaa tagtyattag tttggccgtc ctaatgcatt ttattcgttt gattaagatt  180
ttcttttcat gtatttgtat a                                            201

SEQ ID NO: 42            moltype = DNA  length = 201
FEATURE                  Location/Qualifiers
misc_feature             1..201
                         note = SNP marker
source                   1..201
                         mol_type = genomic DNA
                         organism = Solanum lycopersicum
SEQUENCE: 42
ccaattttat aaaatgagat agttcctcag tattccgtca ctgcttttgt ttaagcttca  60
gtttccacta gcaaacttta cattgttatg ctccatattc gtaataatcc atgaacttaa  120
ctgtttaccg ctctttcctc attgagaaat ggtttaaaac atataacttg tacttttcgc  180
tgcaaacata ttacattgtt t                                            201

SEQ ID NO: 43            moltype = DNA  length = 201
FEATURE                  Location/Qualifiers
misc_feature             1..201
                         note = SNP marker
source                   1..201
                         mol_type = genomic DNA
                         organism = Solanum lycopersicum
SEQUENCE: 43
tacagaagac acaaaatact tcacaccaga ctaaattaca cagacaagca caatcatcag  60
tcctcccaaa tttacagaag accatatcat cacattatgg cacaaccctt cctttcctct  120
tgcggctgtg cggcwgttgg cggatatctg ttcgactccg atgggttgta agtaaactct  180
gatgtgtcaa gtccatactg g                                            201

SEQ ID NO: 44            moltype = DNA  length = 201
FEATURE                  Location/Qualifiers
misc_feature             1..201
                         note = SNP marker
source                   1..201
                         mol_type = genomic DNA
                         organism = Solanum lycopersicum
SEQUENCE: 44
aataaagcaa tcaacagaaa gcaaaccttt tccctcatac gtgtactcca ygcatcattt  60
ctacttggac gattatcaag agtagcagta acagggacac tagttgcagg atttgctggt  120
ggcctattgt tgatcagtgg ctgtcggatt tgttgtctgg gaccacctat gtactcatca  180
tcactatcat artctgctgg t                                            201

SEQ ID NO: 45            moltype = DNA  length = 852
FEATURE                  Location/Qualifiers
misc_feature             1..852
                         note = Tom2a_GNL.3951_R 43637 minus-strand
source                   1..852
                         mol_type = genomic DNA
                         organism = Solanum lycopersicum
SEQUENCE: 45
atggcgtgca aagggtttg ggagtgcttg ttgaagctct tgaacttttt gttgaccctt  60
gttggtttga caatggtggg gtatggtatt tatctatttg ttgagtacaa aaatcattca  120
cactccggag atgattaccc agttgcacca cctatgagtg gtgacatgat agagtttggt  180
cgtccaatgc tgatggctgt atcgttggct gaaaacatat ttgataaact tccaaaacct  240
tggttcatat atttgtttat tggtattgga gcagttcttg tagttgtatc ttgctgtggt  300
tgtattggag caacaaggaa tggttgctgc ctgagttgtt actccatgtt gattttcttg  360
ttgatcttgg tagagctagg tgctgctggt tttatattct ttgataaaag ctggaaagat  420
gaaattccaa gggataaaac gggcaacttt gaaacgatct atgactttct ggatgaccac  480
tggaagatta ttaagtgggt tgcccttggt gctgttatat tcgaggctct tatattctta  540
ttggccctcg tagtaggggc agcaaacaga ccagcagatt atgatagtga tgatgagtac  600
ataggtggtc ccagacaaca aatccgacag ccactgatca acaataggcc accagcaaat  660
cctgcaacta gtgtccctgt tactgctact cttgataatc gtccaagtag aaatgatgca  720
tggagtacac gtatgaggga aaagtatgga cttgacacat cagagtttac ttacaaccca  780
tcggagtcga acagatatcc gccaacagcc gcacagccgc aagaggaaag gaagggttgt  840
gccataatgt ga                                                      852

SEQ ID NO: 46            moltype = AA  length = 283
FEATURE                  Location/Qualifiers
REGION                   1..283
                         note = Tom2a_GNL.3951_R 43637
source                   1..283
                         mol_type = protein
                         organism = Solanum lycopersicum
SEQUENCE: 46
MACKGFWECL LKLLNFLLTL VGLTMVGYGI YLFVEYKNHS HSGDDYPVAP PMSGDMIEFG  60
```

-continued

```
RPMLMAVSLA ENIFDKLPKP WFIYLFIGIG AVLVVVSCCG CIGATRNGCC LSCYSMLIFL  120
LILVVELGAAG FIFFDKSWKD EIPRDKTGNF ETIYDFLDDH WKIIKWVALG AVIFEALIFL  180
LALVVGAANR PADYDSDDEY IGGPRQQIRQ PLINNRPPAN PATSVPVTAT LDNRPSRNDA  240
WSTRMREKYG LDTSEFTYNP SESNRYPPTA AQPQEERKGC AIM                   283

SEQ ID NO: 47          moltype = DNA  length = 855
FEATURE                Location/Qualifiers
misc_feature           1..855
                       note = tom2a_SL3_00_S minus-strand
source                 1..855
                       mol_type = genomic DNA
                       organism = Solanum lycopersicum
SEQUENCE: 47
atggcgtgca aagggttttg ggagtgcttg ttgaagctct tgaacttttt gttgaccctt  60
gttggtttga caatggtggg gtatggtatt tatctatttg ttgagtacaa aaatcattca  120
cactccggag atgattaccc agttgcacca cctatgagtg gtgacatgat agagtttggt  180
cgtccaatgc tgatggctgt atcgttggct gaaaacatat ttgataaact tccaaaacct  240
tggttcatat atttgtttat tggtattgga gcagttcttg tagttgtatc ttgctgtggt  300
tgtattggag cggcaacaag gaatggttgc tgcctgagtt gttactccat gttgattttc  360
ttgttgatct tggtagagct aggtgctgct ggttttatat tctttgataa aagctggaaa  420
gatgaaattc caagggataa aacgggcaac tttgaaacga tctatgactt tctggatgac  480
cactggaaga ttattaagtg ggttgccctt ggtgctgtta tattcgaggc tcttatattc  540
ttattggccc tcgtagtaag ggcagcaaac agaccagcag actatgatag tgatgatgag  600
tacataggtg gtcccagaca acaaatccga cagccactga tcaacaatag gccaccagca  660
aatcctgcaa ctggtgtccc tgttactgct actcttgata atcgtccaag tagaaatgat  720
gcgtggagta cacgtatgag ggaaaagtat ggacttgaca catcagagtt tacttacaac  780
ccatcggagt cgaacagata tccgccaact gccgcacagc cgcaagagga aaggaagggt  840
tgtaccataa tgtga                                                  855

SEQ ID NO: 48          moltype = AA  length = 284
FEATURE                Location/Qualifiers
REGION                 1..284
                       note = Tom2a_SL3_00_S
source                 1..284
                       mol_type = protein
                       organism = Solanum lycopersicum
SEQUENCE: 48
MACKGFWECL LKLLNFLLTL VGLTMVGYGI YLFVEYKNHS HSGDDYPVAP PMSGDMIEFG  60
RPMLMAVSLA ENIFDKLPKP WFIYLFIGIG AVLVVVSCCG CIGAATRNGC CLSCYSMLIF  120
LLILVELGAA GFIFFDKSWK DEIPRDKTGN FETIYDFLDD HWKIIKWVAL GAVIFEALIF  180
LLALVVRAAN RPADYDSDDE YIGGPRQQIR QPLINNRPPA NPATGVPVTA TLDNRPSRND  240
AWSTRMREKY GLDTSEFTYN PSESNRYPPT AAQPQEERKG CTIM                  284

SEQ ID NO: 49          moltype = DNA  length = 20
FEATURE                Location/Qualifiers
misc_feature           1..20
                       note = TBFRV FW 3 Primer
source                 1..20
                       mol_type = genomic DNA
                       organism = Solanum lycopersicum
SEQUENCE: 49
gtacatcttg ctggtcttgt                                             20

SEQ ID NO: 50          moltype = DNA  length = 21
FEATURE                Location/Qualifiers
misc_feature           1..21
                       note = TBFRV RV 3 Primer
source                 1..21
                       mol_type = genomic DNA
                       organism = Solanum lycopersicum
SEQUENCE: 50
cgctctctcc attctcttat c                                           21

SEQ ID NO: 51          moltype = DNA  length = 24
FEATURE                Location/Qualifiers
misc_feature           1..24
                       note = TBFRV P3 Primer
source                 1..24
                       mol_type = genomic DNA
                       organism = Solanum lycopersicum
SEQUENCE: 51
tggtggtgtc agtgtctgtt tggt                                        24

SEQ ID NO: 52          moltype = DNA  length = 21
FEATURE                Location/Qualifiers
misc_feature           1..21
                       note = PHD FW1
source                 1..21
                       mol_type = genomic DNA
```

-continued

```
                        organism = Solanum lycopersicum
SEQUENCE: 52
taccaactct tcctcccata g                                     21

SEQ ID NO: 53           moltype = DNA  length = 18
FEATURE                 Location/Qualifiers
misc_feature            1..18
                        note = PHD RV1
source                  1..18
                        mol_type = genomic DNA
                        organism = Solanum lycopersicum
SEQUENCE: 53
tggatcgcac tgtgagta                                         18

SEQ ID NO: 54           moltype = DNA  length = 24
FEATURE                 Location/Qualifiers
misc_feature            1..24
                        note = PHD P1
source                  1..24
                        mol_type = genomic DNA
                        organism = Solanum lycopersicum
SEQUENCE: 54
ttcaaagact tctccgcccg tcac                                  24
```